US006955888B2

(12) United States Patent
Zerangue et al.

(10) Patent No.: US 6,955,888 B2
(45) Date of Patent: Oct. 18, 2005

(54) METHODS OF SCREENING AGENTS, CONJUGATES OR CONJUGATE MOIETIES FOR TRANSPORT BY A PEPT2 TRANSPORTER

(75) Inventors: Noa Zerangue, San Carlos, CA (US); Tracy Dias, Pleasanton, CA (US); William J Dower, Menlo Park, CA (US)

(73) Assignee: XenoPort, Santa Clara, CA (US)

( * ) Notice: Subject to any disclaimer, the term of this patent is extended or adjusted under 35 U.S.C. 154(b) by 58 days.

(21) Appl. No.: 10/170,217

(22) Filed: Jun. 11, 2002

(65) Prior Publication Data

US 2003/0017964 A1 Jan. 23, 2003

Related U.S. Application Data

(60) Provisional application No. 60/361,002, filed on Mar. 1, 2002, and provisional application No. 60/297,732, filed on Jun. 11, 2001.

(51) Int. Cl.[7] ...................... G01N 33/53; G01N 33/567; C12P 21/06; C12N 1/20
(52) U.S. Cl. ...................... 435/7.2; 435/7.21; 435/69.1; 435/252.3
(58) Field of Search ................................. 435/7.21, 7.1, 435/7.2, 69.1, 252.3, 471; 530/350

(56) References Cited

U.S. PATENT DOCUMENTS 5,710,018 A     1/1998   Dantzig et al.

OTHER PUBLICATIONS

Ayala FJ and Kiger Jr JA. Modern Genetics. p 45–48. James W. Behnke, ed. The Benjamin/Cummings Publishing Co., Menlow Park, CA, 1980.*

Rieger R. et al. Glossary of Genetics:Classical and Molecular. 5th ed. p 16–17, Springer–Verlag, New York, 1991.*
Liu W. et al. Biochimica et Biophysica Acta 1235:461–466, 1995.*
Liang R, et al. J. Biol. Chem. 270(12), 6456–6463, 1995.*
Doring et al., "Delta–aminolevulinic Acid Transport by Intestinal and Renal Peptide Transporters and Its Physiological and Clinical Implications," J. Clin. Invest. 101(12):2761–2767 (1998).
Fei et al., Nature 368: 563–566 (1994).
Miyamoto et al., Biochimica et Biophysica Acta 1305:34–38 (1996).
Liu et al., Biochimica et Biophysica Acta 1235:461–466 (1995).
Boll et al., Prod. Natl. Acad. Sci. USA 93:284–289 (1996).
Saito et al., Biochimica et Biophysica Acta 1280:173–177 (1996).
Iseki et al., Intestinal Absorption of Several β–Lactam Antiobiotics, J. Pharm. Dyn., 7, 768–775 (1984).
Ganapathy et al., Differential Recognition of β–Lactam Antibiotics by Intestinal and Renal Peptide Transporters, PEPT 1 and PEPT 2, The Journal of Biological Chemistry, vol. 270, No. 43, Issue of Oct. 27, pp. 25672–25677, 1995.

(Continued)

Primary Examiner—Robert S. Landsman
(74) Attorney, Agent, or Firm—Townsend and Townsend and Crew LLP

(57) ABSTRACT

The invention provides methods of screening agents, conjugates or conjugate moieties, linked or linkable to agents, for capacity to be transported as substrates through the PEPT2 transporter. The invention also provides methods of treatment involving delivery of agents that either alone, or as a result of linkage to a conjugate moiety, are substrates of the PEPT2 transporter. The invention also provides conjugates comprising a pharmaceutical agent which is linked to a conjugate moiety that is a substrate for a PEPT2 transporter.

12 Claims, 7 Drawing Sheets

OTHER PUBLICATIONS

Siamak A. Adibi, The Oligopeptide Transporter (PEPT–1) in Human Intestine: Biology and Function, Special Reports and Reviews, The American Gastroenterological Association, 1997.

Randall J. Mrsny, Oligopeptide Transporters as Putative Therapeutic Targets for Cancer Cells, Pharmaceutical Research, vol. 15, No. 6, 1998.

Terada et al., Recognition of β–Lactam antibiotics by rat peptide transporters, PEPT1 and PEPT2, in LLC–PK Cells, 1997, The American Physiological Society.

Iseki et al., Multiplicity of the H+ –Dependent Transport Mechanism of Dipeptide and Anionic β–Lactam Antibiotic Ceftibuten in Rat Intestinal Brush–Border Membrane, The Journal of Pharmacology and Experimental Therapeutics, vol. 289, No. 1 (1999).

Kitagawa and Sugaya, Chaacteristics of Uptake of Cefroxadine by Rabbit Small Intestinal Brush Border Membrane Vesicles, Biol. Pharm. Bull. 19(2) 268–273 (1996).

Saitoh et al., Restricted Intestinal Absorption of Some β–Lactam Antibiotics by an Energy–Dependent Efflux System in Rat Intestine, Pharmaceutical Research, vol. 14, No. 5, 1997.

Otto and Bauer, Dipeptide Uptake: A Novel Marker for Testicular and Ovarian Macrophages, The Anatomical Record 245:662–667 1996.

Ganapathy and Liebach, Peptide Transporters, Department of Bochemistry and Molecular Biology, Medical College of Augusta, Georgia, pp. 395–400 (1996).

Zhu et al., Differential Recognition of ACE Inhibitors in Xenopus Laevis Oocytes Expressing Rat PEPT1 and PEPT2, Pharmaceutical Research, vol. 17, No. 5, 2000.

Ganapathy et al., Interaction of Anionic Cephalosporins with the Intestinal and Renal Peptide Transporters PEPT 1 and PEPT2, Biochimica et Biophysica Acta 1324 (1997) 296–308.

Fei et al., Preferential Recognition of Zwitterionic Dipeptides as Transportable Substrates by the High–Affinity Peptide Transporter PEPT2, Biochimica et Biophysica Acta 1418 (1999) 344–351.

Dixon and Mizen, Absorption of Amino Penicillins from Everted Rat Intestine, J. Physiol. (1977), 269, pp. 549–559.

Lee et al., Biopharmaceutics of Transmucosal Peptide and Protein Drug Administration: Role of Transport Mechanisms with a Focus on The Involvement of PEPT1, Journal of Controlled Release 62 (1999) 129–140.

Han et al., CHO/HPEPT1 Cells Overexpressing the Human Peptide Transporter (HPEPT1) as an Alternative in Vitro Model for Peptidomimetic Drugs, Journal of Pharmaceutical Sciences/vol. 88, No. 3, Mar. 1999.

Tamai et al., The Predominant Contributions of Oligopeptide Transporter PEPT1 to Intestinal Absorption of β–Lactam Antiobiotics in the Rat Small Intestine, J. Pharm. Pharmacol. 1997, 49; 796–801.

Ming et al., Human Dipeptide Transporter, Hpept1, Stably Transfected into Chinese Hamster Ovary Cells, Pharmaceutical Research, vol. 13, No. 11, 1996.

Teuscher et al., Functional Evidence for Presence of PEPT2 in Rat Choroid Plexus: *Studies with Glycylsarcosine'*, The Journal of Pharmacology and Experimental Therapeutics, vol. 294, No. 2 (2000).

Terada et al., Characterization of Stably Transfected Kidney Epithelial Cell Line Expressing Rat H+/Peptide Contransporter PEPT1: Localization of PEPT1 and Transport of β–Lactam Antibiotics 1, The Journal of Pharmacology and Experimental Therapeutics, vol. 281, No. 3 (1997).

Gonzales et al., An Oligopeptide Transporter is Expressed at High Levels in the Pancreatic Carcinoma Cell Lines AsPc–1 and Capan–2 1, Cancer Research 58, 519–525. Feb. 1, 1998.

Inui et al., Physiological and Pharmacological Implications of Peptide Transporters, PEPT1 and PEPT2, Nephrology Dialysis Transplantation, Nephrol Dial Transplant (2000) 15 (Suppl 6): 11–13.

Tamai et al., Functional Expression of Transporter for β–Lactam Antibiotics and Dipeptides in Xenopus Laevis Oocytes Injected with Messenger RNA from Human, Rat and Rabbit Small Intestines 1, The Journal of Pharmacology and Experimental Therapeutics, vol. 273, No.1 (1995).

Naasani et al., Comparison of the Transport Characteristics of Ceftibuten in Rat Renal and Intestinal Brush–Border Membranes, Biochimica et Biophysica Acta 1231 (1995) 163–168.

Dantzig et al., Association of Intestinal Peptide Transport with a Protein Related to the Cadherin Superfamily, Science, vol. 264, Apr. 15, 1994.

Yuasa et al., Peptide Carrier–Mediated Transport in Intestinal Brush Border Membrane Vesicles of Rats and Rabbits: Cephradine Uptake and Inhibition, Pharmaceutical Research, vol. 10, No. 3, 1993.

Inui et al., Transepithelial Transport of oral Cephalosporins by Monolayers of Intestinal Epithelial Cell Line Caco–2: Specific Transport Systems in Apical and Basolateral Membranes: The Journal of Pharmacology and Experimental Therapeutics, vol. 261, No. 1 (1992).

Iseki et al., Comparison of Transport Characteristics of Amino β–Lactam Antibiotics and Dipeptides Across Rat Intestinal Brush Border Membrane, J. Pharm. Pharmacol. 1989, 41:628–632.

Dantzig and Bergin, Carrier–Mediated Uptake of Cephalexin in Human Intestinal Cells, Biochemical and Biophysical Research Communications, pp. 1082–1087, vol. 155, No. 2, 1988.

Meredith and Boyd, Structure and Function of Eurkryotic Peptide Transporters, CMLS Cellular and Molecular Life Sciences, CMLS, Cell. Mol. Life Sci. 57 (2000) 754–778.

Ogihara et al., Immuno–Localization of H +/Peptide Cotransporter in Rat Digestive Tract, Biochemical and Biophysical Research Communications 220 848–852 (1996).

Leibach and Ganapathy, Peptide Transporters in the Intestine and the Kidney, Annu. Rev. Nutr. 1996. 16:99–119.

* cited by examiner

SEQUENCE LISTING

```
<160> NUMBER OF SEQ ID NOS: 10

<210> SEQ ID NO 1
<211> LENGTH: 708
<212> TYPE: PRT
<213> ORGANISM: Homo sapiens

<400> SEQUENCE: 1

Met Gly Met Ser Lys Ser His Ser Phe Phe Gly Tyr Pro Leu Ser Ile
1               5                   10                  15

Phe Phe Ile Val Val Asn Glu Phe Cys Glu Arg Phe Ser Tyr Tyr Gly
            20                  25                  30

Met Arg Ala Ile Leu Ile Leu Tyr Phe Thr Asn Phe Ile Ser Trp Asp
        35                  40                  45

Asp Asn Leu Ser Thr Ala Ile Tyr His Thr Phe Val Ala Leu Cys Tyr
    50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
            100                 105                 110

Gly Thr Pro Asp Ser Leu Pro Val His Val Val Leu Ser Leu Ile Gly
        115                 120                 125

Leu Ala Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160
```

```
Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
            180                 185                 190

Ser Lys Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
210                 215                 220

Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
                245                 250                 255

Lys Arg Glu His Trp Leu Asp Trp Ala Lys Glu Lys Tyr Asp Glu Arg
            260                 265                 270

Leu Ile Ser Gln Ile Lys Met Val Thr Arg Val Met Phe Leu Tyr Ile
        275                 280                 285

Pro Leu Pro Met Phe Trp Ala Leu Phe Asp Gln Gln Gly Ser Arg Trp
290                 295                 300

Thr Leu Gln Ala Thr Thr Met Ser Gly Lys Ile Gly Ala Leu Glu Ile
305                 310                 315                 320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
            340                 345                 350

Phe Asn Phe Thr Ser Leu Lys Lys Met Ala Val Gly Met Val Leu Ala
        355                 360                 365

Ser Met Ala Phe Val Val Ala Ala Ile Val Gln Val Glu Ile Asp Lys
    370                 375                 380

Thr Leu Pro Val Phe Pro Lys Gly Asn Glu Val Gln Ile Lys Val Leu
385                 390                 395                 400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
            420                 425                 430

Asn Lys Leu Thr Arg Ile Asn Ile Ser Ser Pro Gly Ser Pro Val Thr
        435                 440                 445

Ala Val Thr Asp Asp Phe Lys Gln Gly Gln Arg His Thr Leu Leu Val
    450                 455                 460

Trp Ala Pro Asn His Tyr Gln Val Val Lys Asp Gly Leu Asn Gln Lys
465                 470                 475                 480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
            500                 505                 510

Tyr Asn Ala Ser Thr Tyr Gln Phe Phe Pro Ser Gly Ile Lys Gly Phe
        515                 520                 525

Thr Ile Ser Ser Thr Glu Ile Pro Pro Gln Cys Gln Pro Asn Phe Asn
    530                 535                 540

Thr Phe Tyr Leu Glu Phe Gly Ser Ala Tyr Thr Tyr Ile Val Gln Arg
545                 550                 555                 560

Lys Asn Asp Ser Cys Pro Glu Val Lys Val Phe Glu Asp Ile Ser Ala
                565                 570                 575
```

-continued

```
Asn Thr Val Asn Met Ala Leu Gln Ile Pro Gln Tyr Phe Leu Leu Thr
            580                 585                 590

Cys Gly Glu Val Val Phe Ser Val Thr Gly Leu Glu Phe Ser Tyr Ser
        595                 600                 605

Gln Ala Pro Ser Asn Met Lys Ser Val Leu Gln Ala Gly Trp Leu Leu
    610                 615                 620

Thr Val Ala Val Gly Asn Ile Ile Val Leu Ile Val Ala Gly Ala Gly
625                 630                 635                 640

Gln Phe Ser Lys Gln Trp Ala Glu Tyr Ile Leu Phe Ala Ala Leu Leu
                645                 650                 655

Leu Val Val Cys Val Ile Phe Ala Ile Met Ala Arg Phe Tyr Thr Tyr
            660                 665                 670

Ile Asn Pro Ala Glu Ile Glu Ala Gln Phe Asp Glu Asp Glu Lys Lys
        675                 680                 685

Asn Arg Leu Glu Lys Ser Asn Pro Tyr Phe Met Ser Gly Ala Asn Ser
    690                 695                 700

Gln Lys Gln Met
705
```

<210> SEQ ID NO 2
<211> LENGTH: 729
<212> TYPE: PRT
<213> ORGANISM: Homo sapiens

<400> SEQUENCE: 2

```
Met Asn Pro Phe Gln Lys Asn Glu Ser Lys Glu Thr Leu Phe Ser Pro
1               5                   10                  15

Val Ser Ile Glu Glu Val Pro Arg Pro Ser Pro Pro Lys Lys
            20                  25                  30

Pro Ser Pro Thr Ile Cys Gly Ser Asn Tyr Pro Leu Ser Ile Ala Phe
        35                  40                  45

Ile Val Val Asn Glu Phe Cys Glu Arg Phe Ser Tyr Tyr Gly Met Lys
    50                  55                  60

Ala Val Leu Ile Leu Tyr Phe Leu Tyr Phe Leu His Trp Asn Glu Asp
65                  70                  75                  80

Thr Ser Thr Ser Ile Tyr His Ala Phe Ser Ser Leu Cys Tyr Phe Thr
                85                  90                  95

Pro Ile Leu Gly Ala Ala Ile Ala Asp Ser Trp Leu Gly Lys Phe Lys
            100                 105                 110

Thr Ile Ile Tyr Leu Ser Leu Val Tyr Val Leu Gly His Val Ile Lys
        115                 120                 125

Ser Leu Gly Ala Leu Pro Ile Leu Gly Gly Gln Val Val His Thr Val
    130                 135                 140

Leu Ser Leu Ile Gly Leu Ser Leu Ile Ala Leu Gly Thr Gly Gly Ile
145                 150                 155                 160

Lys Pro Cys Val Ala Ala Phe Gly Gly Asp Gln Phe Glu Glu Lys His
                165                 170                 175

Ala Glu Glu Arg Thr Arg Tyr Phe Ser Val Phe Tyr Leu Ser Ile Asn
            180                 185                 190

Ala Gly Ser Leu Ile Ser Thr Phe Ile Thr Pro Met Leu Arg Gly Asp
        195                 200                 205

Val Gln Cys Phe Gly Glu Asp Cys Tyr Ala Leu Ala Phe Gly Val Pro
    210                 215                 220

Gly Leu Leu Met Val Ile Ala Leu Val Val Phe Ala Met Gly Ser Lys
225                 230                 235                 240
```

```
-continued

Ile Tyr Asn Lys Pro Pro Glu Gly Asn Ile Val Ala Gln Val Phe
            245                 250                 255

Lys Cys Ile Trp Phe Ala Ile Ser Asn Arg Phe Lys Asn Arg Ser Gly
        260                 265                 270

Asp Ile Pro Lys Arg Gln His Trp Leu Asp Trp Ala Glu Lys Tyr
            275                 280                 285

Pro Lys Gln Leu Ile Met Asp Val Lys Ala Leu Thr Arg Val Leu Phe
290                 295                 300

Leu Tyr Ile Pro Leu Pro Met Phe Trp Ala Leu Leu Asp Gln Gly
305                 310                 315                 320

Ser Arg Trp Thr Leu Gln Ala Ile Arg Met Asn Arg Asn Leu Gly Phe
                325                 330                 335

Phe Val Leu Gln Pro Asp Gln Met Gln Val Leu Asn Pro Leu Leu Val
            340                 345                 350

Leu Ile Phe Ile Pro Leu Phe Asp Phe Val Ile Tyr Arg Leu Val Ser
            355                 360                 365

Lys Cys Gly Ile Asn Phe Ser Ser Leu Arg Lys Met Ala Val Gly Met
    370                 375                 380

Ile Leu Ala Cys Leu Ala Phe Ala Val Ala Ala Val Glu Ile Lys
385                 390                 395                 400

Ile Asn Glu Met Ala Pro Ala Gln Pro Gly Pro Gln Glu Val Phe Leu
                405                 410                 415

Gln Val Leu Asn Leu Ala Asp Asp Glu Val Lys Val Thr Val Val Gly
            420                 425                 430

Asn Glu Asn Asn Ser Leu Leu Ile Glu Ser Ile Lys Ser Phe Gln Lys
        435                 440                 445

Thr Pro His Tyr Ser Lys Leu His Leu Lys Thr Lys Ser Gln Asp Phe
    450                 455                 460

His Phe His Leu Lys Tyr His Asn Leu Ser Leu Tyr Thr Glu His Ser
465                 470                 475                 480

Val Gln Glu Lys Asn Trp Tyr Ser Leu Val Ile Arg Glu Asp Gly Asn
                485                 490                 495

Ser Ile Ser Ser Met Met Val Lys Asp Thr Glu Ser Arg Thr Thr Asn
            500                 505                 510

Gly Met Thr Thr Val Arg Phe Val Asn Thr Leu His Lys Asp Val Asn
        515                 520                 525

Ile Ser Leu Ser Thr Asp Thr Ser Leu Asn Val Gly Glu Asp Tyr Gly
    530                 535                 540

Val Ser Ala Tyr Arg Thr Val Gln Arg Gly Glu Tyr Pro Ala Val His
545                 550                 555                 560

Cys Arg Thr Glu Asp Lys Asn Phe Ser Leu Asn Leu Gly Leu Leu Asp
                565                 570                 575

Phe Gly Ala Ala Tyr Leu Phe Val Ile Thr Asn Thr Asn Gln Gly
            580                 585                 590

Leu Gln Ala Trp Lys Ile Glu Asp Ile Pro Ala Asn Lys Met Ser Ile
        595                 600                 605

Ala Trp Gln Leu Pro Gln Tyr Ala Leu Val Thr Ala Gly Glu Val Met
    610                 615                 620

Phe Ser Val Thr Gly Leu Glu Phe Ser Tyr Ser Gln Ala Pro Ser Gly
625                 630                 635                 640

Met Lys Ser Val Leu Gln Ala Ala Trp Leu Leu Thr Ile Ala Val Gly
                645                 650                 655
```

```
Asn Ile Ile Val Leu Val Val Ala Gln Phe Ser Gly Leu Val Gln Trp
            660                 665                 670
Ala Glu Phe Ile Leu Phe Ser Cys Leu Leu Leu Val Ile Cys Leu Ile
        675                 680                 685
Phe Ser Ile Met Gly Tyr Tyr Tyr Val Pro Val Lys Thr Glu Asp Met
    690                 695                 700
Arg Gly Pro Ala Asp Lys His Ile Pro His Ile Gln Gly Asn Met Ile
705                 710                 715                 720
Lys Leu Glu Thr Lys Lys Thr Lys Leu
                725

<210> SEQ ID NO 3
<211> LENGTH: 26
<212> TYPE: DNA
<213> ORGANISM: Artificial
<220> FEATURE:
<223> OTHER INFORMATION: PEPT1 #1 Forward primer

<400> SEQUENCE: 3
catgcaccac cacgcccagc tatttt                                   26

<210> SEQ ID NO 4
<211> LENGTH: 26
<212> TYPE: DNA
<213> ORGANISM: Artificial
<220> FEATURE:
<223> OTHER INFORMATION: PEPT1 #1 Reverse primer

<400> SEQUENCE: 4
gcgcggtagc tcaagcctgt aatccc                                   26

<210> SEQ ID NO 5
<211> LENGTH: 26
<212> TYPE: DNA
<213> ORGANISM: Artificial
<220> FEATURE:
<223> OTHER INFORMATION: PEPT1 #2 Forward primer

<400> SEQUENCE: 5
ccgcgttgct tctggtcgtc tgtgta                                   26

<210> SEQ ID NO 6
<211> LENGTH: 26
<212> TYPE: DNA
<213> ORGANISM: Artificial
<220> FEATURE:
<223> OTHER INFORMATION: PEPT1 #2 Reverse primer

<400> SEQUENCE: 6
tccatcctcc acttgcctcc tgacct                                   26

<210> SEQ ID NO 7
<211> LENGTH: 26
<212> TYPE: DNA
<213> ORGANISM: Artificial
<220> FEATURE:
<223> OTHER INFORMATION: PEPT2 #1 Forward primer

<400> SEQUENCE: 7
acaaccaatg ggatgacaac cgtgag                                   26

<210> SEQ ID NO 8
<211> LENGTH: 26
<212> TYPE: DNA
```

-continued

```
<213> ORGANISM: Artificial
<220> FEATURE:
<223> OTHER INFORMATION: PEPT2 #1 Reverse primer

<400> SEQUENCE: 8
aggcagatca ccagcaggag gcagga                                            26

<210> SEQ ID NO 9
<211> LENGTH: 26
<212> TYPE: DNA
<213> ORGANISM: Artificial
<220> FEATURE:
<223> OTHER INFORMATION: PEPT2 #2 Forward primer

<400> SEQUENCE: 9
caatgttggt gaagactatg gtgtgt                                            26

<210> SEQ ID NO 10
<211> LENGTH: 26
<212> TYPE: DNA
<213> ORGANISM: Artificial
<220> FEATURE:
<223> OTHER INFORMATION: PEPT2 #2 Reverse primer

<400> SEQUENCE: 10
aacaagcacg atgatattcc caactg                                            26
```

METHODS OF SCREENING AGENTS, CONJUGATES OR CONJUGATE MOIETIES FOR TRANSPORT BY A PEPT2 TRANSPORTER

CROSS-REFERENCE TO RELATED APPLICATIONS

The present application derives priority from U.S. Ser. No. 60/361,002, filed Mar. 1, 2002 and U.S. Ser. No. 60/297,732 filed on 11 Jun. 2001, both incorporated by reference in their entirety for all purposes.

BACKGROUND OF THE INVENTION

Recent advances in the pharmaceutical industry have resulted in the formation of an increasing number of potential therapeutic agents. However, formulating the compounds for effective oral bioavailability has proven difficult because of problems associated with uptake and high susceptibility to metabolic enzymes.

Natural transporter proteins are involved in the uptake of various molecules into and/or through cells. In general, two major transport systems exist: solute carrier-mediated systems and receptor mediated systems. Carrier-mediated systems use transport proteins that are anchored to the cell membrane, typically by a plurality of membrane-spanning loops and function by transporting their substrates via an energy-dependent flip-flop or other mechanism, exchange and other facilitative or equilibrative mechanisms. Carrier-mediated transport systems are involved in the active or non-active, facilitated transport of many important nutrients such as vitamins, sugars, and amino acids. The carrier systems result in transport into the enterocytes from blood or lumen, and across the epithelial cell layer from lumen into blood (absorption) or blood to lumen (secretion). Carrier-mediated transporters are also present in organs such as the liver and kidney, in which the proteins are involved in the excretion or re-absorption of circulating compounds.

Receptor-mediated transport systems differ from the carrier-mediated systems in that these systems usually utilize proteins that span the cell membrane only a single time. Furthermore, substrate binding triggers an invagination and encapsulation process that results in the formation of various transport vesicles to carry the substrate (and sometimes other molecules) into and through the cell. This process of membrane deformations that result in the internalization of certain substrates and their subsequent targeting to certain locations in the cytoplasm is generally referred to as endocytosis.

Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the intestinal epithelia. This transport is frequently energized by co-transport of ions down a concentration gradient.

Known examples of solute carrier systems include two peptide transporters, PEPT1 and PEPT2. The endogenous substrates for these transporters are small peptides consisting of two or three amino acids. These transporters function in the absorption of peptides arising from the digestion of dietary proteins (small intestine) and in the reabsorption of peptides present in the glomerular filtrate.

The human intestinal peptide transporter (PEPT1) and the human kidney peptide transporter (PEPT2) exhibit about 48% identity at the amino acid level. Neither peptide transporter shows significant sequence identity to other known mammalian sequences- they are both about 20% identical to PHT1 and PHT2. The two transporters show some differences in the recognition of β-lactam antibiotics as substrates as well as their marked differences in affinity for many substrates. As such, PEPT1 is a high capacity, low-affinity transporter and PEPT2 is a high affinity transporter. Both transporters accept small peptides as substrates and are driven by a transmembrane electrochemical H+ gradient.

PEPT1 and PEPT2 have been reported to show different patterns of expression in different human tissues. PEPT1 has been reported to be expressed predominantly in the intestine, and also in the kidney (pars convoluta), and liver, with small amounts of expression in the brain and pancreas. Fei et al., *Nature* 386:563–566 (1994) and Miyamoto et al., *Biochimica et Biophysica Acta* 1305:34–38 (1996). By contrast, PEPT2 has been reported to be expressed in the kidney and brain, with lower expression reported in the lung, liver and heart and no expression reported in the small intestine. Liu et al., *Biochimica et Biophysica Acta* 1235:461–466 (1995) and Boll et al., *Proc. Natl. Acad. Sci. USA* 93:284–289 (1996) and Saito et al., *Biochimica et Biophysica Acta* 1280:173–177 (1996). Because of the view that PEPT1 and not PEPT2 is expressed in the intestine, existing efforts to improve oral delivery of drugs via peptide transporters have focused on identifying pharmacological agents that are, or can be modified to be, substrates for PEPT1.

SUMMARY OF THE CLAIMED INVENTION

The present invention provides a conjugate comprising a pharmaceutical agent which is linked to a conjugate moiety that is a substrate for a PEPT2 transporter. The conjugate has a Vmax of at least 1% of Gly-Sar for the PEPT2 transporter. The conjugate has a greater Vmax for PEPT2 than the pharmaceutical agent alone, i.e., without the conjugate moiety.

Preferably, the conjugate has a Vmax for the PEPT2 transporter of at least 5%, more preferably at least 10%, even more preferably at least 20%, still more preferably at least about 50%, and most preferably at least 100%, respectively, of the Vmax of substrate Gly-Sar for PEPT2.

Preferably, the pharmaceutical agent without the conjugate moiety has a Vmax for the PEPT2 transporter of less than 1% of the Vmax of substrate Gly-Sar for PEPT2.

Preferably, the ratio of Vmax between the conjugate and Gly-Sar is greater for the PEPT2 transporter than for the PEPT1 transporter, more preferably the ratio for the PEPT2 transporter is at least twice, even more preferably at least 10 times, and most preferably at least 100 times, respectively, of the ratio for the PEPT1 transporter.

The present invention also provides a method of treatment comprising administering a pharmacologically effective amount of the conjugate to a patient as well as a method of making a pharmaceutical composition comprising formulating the conjugate with a pharmaceutically acceptable carrier.

The present invention further provides a method of screening pharmaceutical agents, conjugates and/or conjugate moieties for pharmacological administration. The method includes providing cell(s) expressing PEPT2 transporter, contacting the cell(s) with the agent, conjugate or moiety and determining whether the agent, conjugate, or moiety passes into and/or through the cell by way of the transporter. Preferably, the cell(s) is transfected with DNA encoding the PEPT2 transporter. More preferably, the cell(s) is an oocyte injected with nucleic acid encoding the PEPT2 transporter. Even more preferably, the cell(s) exhibits no detectable PEPT1 receptor.

The invention also provides methods of manufacturing a pharmaceutical composition. Such method include linking an agent to a conjugate moiety to form a conjugate wherein the conjugate is transported by the PEPT2 transporter with a Vmax of at least 1% of the Vmax of the substrate Gly-Sar. The conjugate is then formulated with a carrier as a pharmaceutical composition.

BRIEF DESCRIPTIONS OF THE FIGURES

DEFINITIONS

Figure 1:
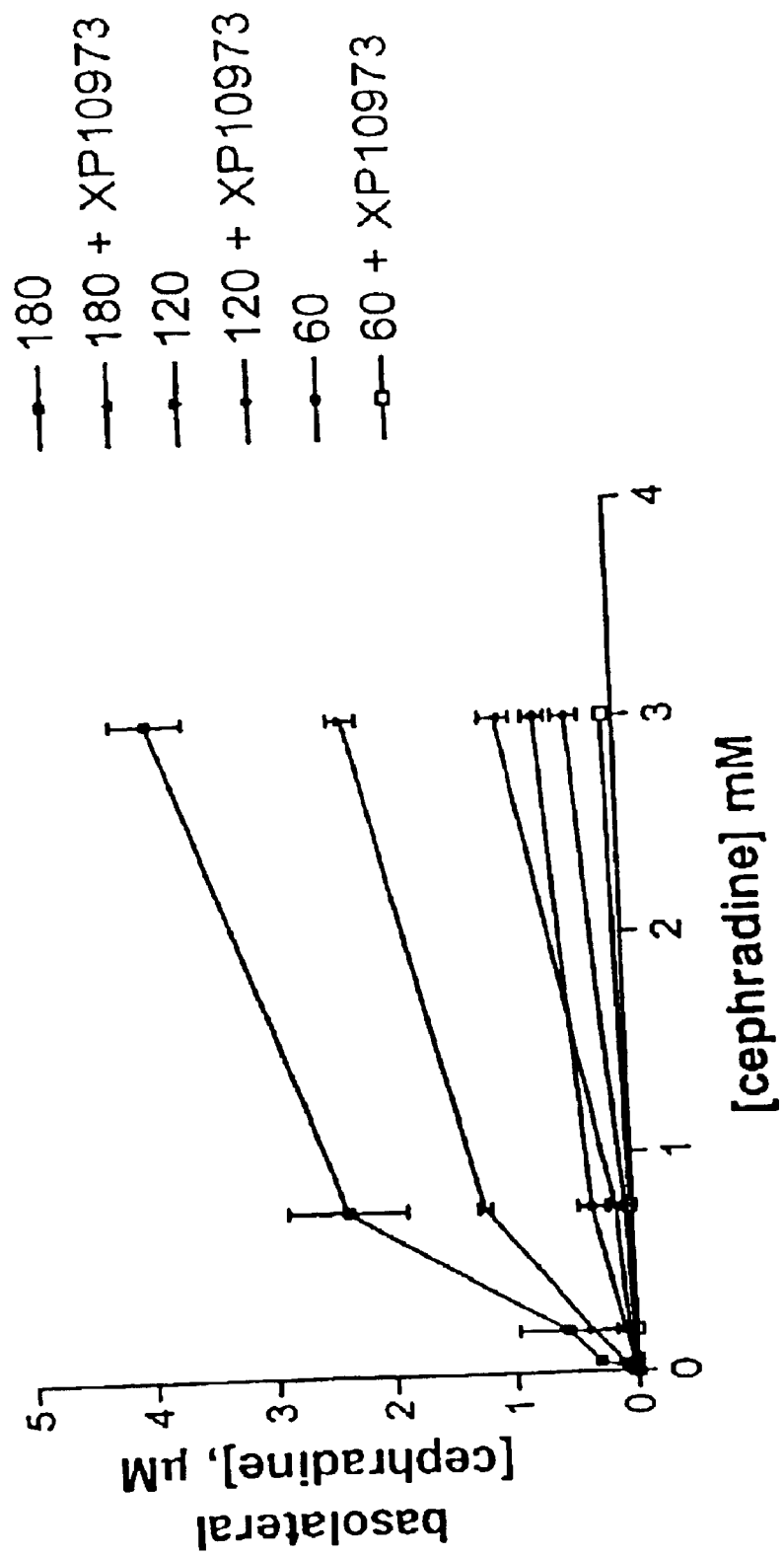
FIG. 1 shows uptake of cephradine by Caco-2 cells.

The phrases "specifically binds" when referring to a protein or "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule such as an antibody that specifically binds to a protein often has an association constant of at least $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. However, some substrates of transporter, PEPT1 in particular, have much lower affinities of the order of $10–10^3$ $M^{-1}$ and yet the binding can still be shown to be specific. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) "Antibodies, A Laboratory Manual", Cold Spring Harbor Publications, New York, for a description of immunoassay formats and conditions that can be used to determine specific immunoreactivity.

A "transport protein" is a protein that has a direct or indirect role in transporting a molecule into and/or through a cell. The term includes, for example, membrane-bound proteins that recognize a substrate and effects its entry into, or exit from a cell by a carrier-mediated transporter or by receptor-mediated transport. These proteins are sometimes referred to as transporter proteins. The term also includes intracellularly expressed proteins that participate in trafficking of substrates through or out of a cell. The term also includes proteins or glycoproteins exposed on the surface of a cell that do not directly transport a substrate but bind to the substrate holding it in proximity to a receptor or transporter protein that effects entry of the substrate into or through the cell. Examples of carrier proteins include: the intestinal and liver bile acid transporters, dipeptide transporters, oligopeptide transporters, simple sugar transporters (e.g., SGLT1), phosphate transporters, monocarboxcylic acid transporters, transporters comprising P-glycoproteins, organic anion transporters (OATP), and organic cation transporters. Examples of receptor-mediated transport proteins include: viral receptors, immunoglobulin receptors, bacterial toxin receptors, plant lectin receptors, bacterial adhesion receptors, vitamin transporters and cytokine growth factor receptors.

A "substrate" of a transport protein is a compound whose uptake into or passage through a cell is facilitated by the transport protein.

The term "ligand" of a transport protein includes substrates and other compounds that bind to the transport protein without being taken up or transported through a cell. Some ligands by binding to the transport protein inhibit or antagonize uptake of the substrate or passage of substrate through a cell by the transport protein. Some ligands by binding to the transport protein promote or agonize uptake or passage of the compound by the transport protein or another transport protein. For example, binding of a ligand to one transport protein can promote uptake of a substrate by a second transport protein in proximity with the first transport protein.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

An agent is "orally active" if it can exert a phamalogical activity when administered via an oral route.

A "conjugate moiety" refers to a compound or part of a compound that does not itself have pharmacological activity but which can be linked to an agent to form a conjugate that does have pharmacological activity. Typically, the agent has pharmacologic activity without the conjugate moiety. The conjugate moiety facilitates therapeutic use of the agent by promoting uptake of the agent via a transporter. A conjugate moiety can itself be a substrate for a transporter or can become a substrate when linked to a compound (e.g., valacyclovir). Thus, a conjugate moiety formed from a compound and a conjugate moiety can have higher uptake activity than either the compound or moiety alone.

A "pharmacological" activity means that an agent at least exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

Vmax and Km of a compound for a transporter are defined in accordance with convention. Vmax is the number of molecules of compound transported per second at saturating concentration of the compound. Km is the concentration of the compound at which the compound is transported at half of Vmax. In general, a high value of Vmax is desirable for a substrate of a transporter. A low value of Km is desirable for transport of low concentrations of a compound, and a high value of Km is desirable for transport of high concentrations of a compound. Vmax is affected both by the intrinsic turnover rate of a transporter (molecules/transporter protein) and transporter density in plasma membrane that depends on expression level. For these reasons, the intrinsic capacity of a compound to be transported by a particular transporter is usually expressed as the ratio Vmax of the compound/Vmax of a control compound known to be a substrate for the transporter.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Soc. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A transporter is expressed in a particular tissue, e.g., the jejunum, when expression can be detected by mRNA analysis, protein analysis, antibody histochemistry, or functional transport assays. Typically, detectable mRNA expression is at a level of at least 0.01% of that of beta actin in the same tissue. Preferred transporters exhibit levels of expression in the desired tissue of at least 0.1, or 1 or 10% of that of beta actin. Conversely a transporter is not expressed in a particular tissue (e.g., the descending colon) if expression is not detectable above experimental error by any of the above techniques. Thus, transporters that are not expressed in particular tissue exhibit express levels less than 0.1% of beta actin, and usually less than 0.01% of beta actin.

Sustained release refers to release of a therapeutic or prophylactic amount of the drug or an active metabolite thereof into the systemic blood circulation over a prolonged period of time relative to that achieved by oral administration of a conventional formulation of the drug.

DETAILED DESCRIPTION OF THE INVENTION

1. Introduction

The invention provides methods of screening agents, conjugates or conjugate moieties, linked or linkable to agents, for capacity to be transported as substrates through the PEPT2 transporter. The invention also provides methods of treatment involving oral delivery of agents that either alone, or as a result of linkage to a conjugate moiety, are substrates of the PEPT2 transporter. The present methods are premised, in part, on the inventors' results showing that PEPT2 is expressed in the human intestine, particularly the stomach, jejunum, ileum, the ileo-caecal valve, the cecum and the ascending colon. Previous workers have reported that PEPT2 is present in the brain and kidney but is absent from the intestine. It is believed that the discrepancy between the present results and previous work may be because most previous work to determine tissues in which PEPT2 is expressed was performed on the rat rather than the human, and because of the greater sensitivity of detection of quantitative PCR employed in the present examples.

The insight that PEPT2 is expressed in the human intestine opens up new strategies for design and delivery of drugs through this transporter. Because of the different substrate specificities of PEPT1 and PEPT2, some agents, conjugates or conjugate moieties that are poor substrates for PEPT1 are transported to a greater extent by PEPT2. Therefore, the availability of PEPT2 as an alternative transporter to PEPT1 broadens the range of agents, conjugates and conjugate moieties that can pass through or facilitate passage through the intestine. Therefore, agents, conjugates or conjugate moieties that are found to be poorly transported by PEPT1 in screening assays should not necessarily be discarded but can be retested for transport via PEPT2. Agents, conjugates or conjugate moieties can also be designed or screened with PEPT2 as the intended target. Expression of PEPT2 in the kidney can result in recirculation of agents or conjugates for PEPT2 from the kidney back into the systemic circulation. Reuptake increases the half-life of a drug or conjugate moiety and hence reduces the dosage that need be administered. An advantage of PEPT2 is that its higher affinity for substrates allows testing of candidate substrates at lower concentrations of the candidate substrates than PEPT1. For candidate substrates that are available in only small amounts or which have low solubilities, the ability to determine substrate properties at low concentration of substrate is a significant advantage.

2. PEPT1 and PEPT2

Human PEPT1 has been cloned as a cDNA of 2263 bp with an open reading frame of 2127 bp encoding a protein of 708 amino acids (SEQ ID NO:1) by Liang, *Journal of Biological Chemistry* 270: 6456–6463 (1995). Reference to PEPT1 includes the amino acid sequence of Liang, allelic, cognate and induced variants thereof. Usually such variants show at least 90% sequence identity to the exemplary sequence of Liang. Cognate forms of the human PEPT1 sequence have been cloned from rabbit, and rat tissues. Fei, *Nature* 368: 563–566 (1994), and Miyamoto, *Biochimica et Biophysica Acta* 1305: 34–38 (1996), respectively.

Human PEPT2 has been cloned by Liu et al., *Biochimica et Biophysica Acta* 1235:461–466 (1995). Reference to PEPT2 includes the amino acid sequence of Liu et al. (SEQ ID NO:2), allelic cognate and induced variants thereof. Usually such variants show at least 90% sequence identity to the exemplary sequence of Liu. Saito et al., *Biochimica et Biophysica Acta* 1280, 173–177 (1996) have described the isolation of cDNA encoding the rat H+-coupled peptide transporter PEPT2. The PEPT2 cDNA had 3938 bp, which encoded a 729-amino acid protein of a molecular mass of 81 kDa. The overall amino acid identity was 48% identical to the rat PEPT1. The rat PEPT2 has twelve putative membrane-spanning α-helices and four potential N-linked glycosylation sites at a predicted large extracellular loop between α-helices 9 and 10. The rat PEPT2 showed 83% amino acid identity to the human PEPT2. The experiments described in the Examples show that human PEPT2 is expressed in the kidney, pancreas, liver, brain, lungs, ileum, jejunum and duodenum among other tissues. PEPT2 is also expressed in the CaCo2 cell line that derives from intestinal cells.

3. Methods of Identifying Agents, Conjugates or Conjugate Moieties that are Substrates of the PEPT2 Receptor Agents known or suspected to have pharmacological activity can be screened directly for their capacity to act as substrates of the PEPT2 transporter. Alternatively, conjugate moieties can be screened as substrates, and the conjugate moieties linked to agents having known or suspected pharmacological activity. In such methods, the conjugate moieties can be linked to an agent or other molecule as a conjugate during the screening process. If another molecule is used, the molecule is sometimes chosen to resemble the structure of an agent ultimately intended to be linked to the conjugate moiety for pharmaceutical use. The screening is typically performed on cells expressing the PEPT2 transporter. In some methods, the cells are transfected with DNA encoding the PEPT2 transporter. In other methods, natural cells expressing the PEPT2 transporter are used. In some methods, PEPT2 is the only transporter or the only peptide transporter expressed. In other methods, cells express PEPT2 in combination with other transporters. For example, in some methods, cells expressing both PEPT1 and PEPT2 are used. In still other methods, agents, conjugates or conjugate moieties are screened on different cells expressing different transporters. For example, agents or conjugates can be screened on cells expressing PEPT2 and on cells expressing PEPT1. Methods of screening agents, conjugates or conjugate moieties for passage through cells bearing a transporter are described in WO 01/20331.

Internalization of a compound evidencing passage through transporters can be detected by detecting a signal from within a cell from any of a variety of reporters. The reporter can be as simple as a label such as a fluorophore, a chromophore, a radioisotope, Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In some methods, multiple agents, conjugates or conjugate moieties are screened simultaneously and the identity of each agent or conjugate moiety is tracked using tags linked to the agents, conjugates or conjugate moieties. In some methods, a preliminary step is performed to determine binding of an agent or conjugate moiety to PEPT2. Although not all agents or conjugates that bind PEPT2 are substrates of the transporter, observation of binding is an indication that allows one to reduce the number of candidate substrates from an initial repertoire. In some methods, substrate capacity of an agent or conjugate moiety is tested in comparison with a reference substrate of PEPT2. The artificial dipeptide Gly-Sar has often been used as a reference for PEPT1, and can also be used as a reference for PEPT2. The comparison can either be performed in separate parallel assays in which an agent or conjugate moiety under test and Gly-Sar are compared for uptake on separate samples of the same cells. Alternatively, the comparison can be performed in a competition format in which an agent or conjugate moiety under test and Gly-Sar are applied to the same cells. Typically, the agent or conjugate moiety and Gly-Sar are differentially labeled in such assays.

In such comparative assays, the Vmax of an agent, conjugate moiety, or conjugate comprising an agent and conjugate moiety tested can be compared with that of Gly-Sar. If an agent, conjugate moiety or conjugate has a Vmax of at least 1%, preferably at least 5%, more preferably at least 10%, even more preferably at least 20%, and most preferably at least 50% of Gly-Sar for the PEPT2 transporter then the agent, conjugate moiety or conjugate can be considered to be a substrate for PEPT2. In general, the higher the Vmax of the agent, conjugate moiety or conjugate relative to that of Gly-Sar the better. Therefore, agents, conjugate moieties or conjugates having Vmax's of at least 50%, 100%, 150% or 200% of the Vmax of Gly-Sar for PEPT2 are screened in some methods. The agents to which conjugate moieties are linked can by themselves show little or no detectable substrate activity for PEPT2 (e.g., Vmax relative to that of Gly-Sar of less than 0.1 or 1%).

In some methods, the Vmax of an agent, conjugate moiety or conjugate is also determined relative to Gly-Sar for the transporter PEPT1. Such screening may reveal that the agent, conjugate moiety or conjugate is a better substrate for PEPT2 than PEPT1. The relative capacities of a substrate for PEPT2 and PEPT1 can be compared by a comparison of the ratios of Vmax of the agent, conjugate moiety or conjugate and Gly-Sar for the respective transporters. For example, if the ratio of Vmax's for the agent, conjugate moiety or conjugate to Gly-Sar is greater for PEPT2 than for PEPT1 then the agent, conjugate moiety or conjugate is a better substrate for PEPT2 than for PEPT1. In some methods, the ratio of Vmax's is at least 2, 10, 20, 50, or 100 times greater for PEPT2 than for PEPT1. In some methods, the ratio of the agent, conjugate moiety or conjugate to Gly-Sar for PEPT1 is less than 0.1, 1 or 10% In other methods, the agent, conjugate moiety or conjugate is a substrate for PEPT1 (Vmax of at least 10%, 50%, 100%, 150% or 200% of the Vmax of Gly-Sar for PEPT1. Robust assays are available for both PEPT1 and PEPT2, allowing design and characterization of compounds with substrate (or inhibitor) activities for either PEPT1 or PEPT2, or both. Based on the conventional wisdom, compounds lacking substrate activity on PEPT1 would be rejected as candidates for oral delivery; however, based on our detection of significant PEPT2 expression in human intestine, compounds transported by PEPT2 can be recognized and optimized for oral delivery through PEPT2 transporters in the human intestine).

4. Agents, Conjugates and Conjugate Moieties to be Screened

Compounds constituting agents, conjugates or conjugate moieties to be screened can be naturally occurring or synthetic molecules. Natural sources include sources such as, e.g., marine microorganisms, algae, plants, and fungi. Alternatively, compounds to be screened can be from combinatorial libraries of agents, including peptides or small molecules, or from existing repertories of chemical compounds synthesized in industry, e.g., by the chemical, pharmaceutical, environmental, agricultural, marine, cosmeceutical, drug, and biotechnological industries. Compounds can include, e.g., pharmaceuticals, therapeutics, environmental, agricultural, or industrial agents, pollutants, cosmeceuticals, drugs, organic compounds, lipids, glucocorticoids, antibiotics, peptides, sugars, carbohydrates, and chimeric molecules.

A variety of methods are available for producing peptide libraries (see, e.g., Lam et al., Nature, 354: 82,1991 and WO 92/00091; Geysen et al, J Immunol Meth, 102: 259, 1987: Houghten et al, Nature, 354: 84, 1991 and WO 92/09300 and Lebl et al., Int J Pept Prot Res, 41, 201, 1993). Peptide libraries can also be generated by phage display methods. See, e.g., Dower, U.S. Pat. No. 5,723,286.

Combinatorial libraries can be produced for many types of compounds that can be synthesized in a step-by-step fashion (see e.g. Ellman & Bunin, J Amer Chem Soc, 114:10997, 1992 (benzodiazepine template), WO 95/32184 (oxazolone and aminidine template), WO 95/30642 (dihydrobenzopyran template) and WO 95/35278 (pyrrolidine template). Libraries of compounds are usually synthesized by solid phase chemistry on particle. However, solution-phase library synthesis can also be useful. Strategies for combinatorial synthesis are described by Dol+ Le & Nelson, J. Combinatorial Chemistry 1. 235–282 (1999)) (incorporated by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth. Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. These methods are particularly amenable for tagging as described in more detail below. The size of libraries generated by such methods can vary from 2 different compounds to $10^4$, $10^6$, $10^8$, or $10^{10}$, or any range therebetween.

Preparation of encoded libraries is described in a variety of publications including Needels, et al., Proc. Natl. Acad. Sci. USA 1993, 90, 10700; Ni, et al., J. Med. Chem. 1996, 39, 1601, WO 95/12608, WO 93/06121, WO 94/08051, WO 95/35503 and WO 95/30642 (each of which is incorporated by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both.

Compounds synthesizable by such methods include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Prepared combinatorial libraries are also available from commercial sources (e.g., ChemRx, South San Francisco, Calif.).

Some compounds to be screened are variants of known transporter substrates. The natural function of these transporters is to transport peptides arising from the digestion of dietary proteins (small intestine) and prevent loss of peptides in the glomerular filtrate (kidney). Some compounds to be screened are peptides, variants of amino acids, zwitterionic antibiotics, sugars or nucleosides, or structural variants of any of these. Compounds to be screened also include variants of known substrates, such as β-lactam antibiotics, the anti-cancer agent Bestatin, and angiotensin converting enzyme (ACE) inhibitors. Orally bioavailable antibiotics interact differently with PEPT1 and PEPT2. In general, although not invariably, β-lactam antibiotics having an α-amino group (cefadroxil, cephradine, amoxacillin, and cyclacillin) are better substrates for PEPT2 than PEPT1. β-lactam antibiotics without α-amino groups (ceftibuten, cefixime, and cefdinir) are not as good substrates for PEPT2, but are moderate substrates for PEPT1.

5. Linkage of Agents to Conjugate Moieties

Conjugate moieties that are substrates for PEPT2 or other transporter can be attached to or incorporated into agents having pharmacological activity by a variety of means. Conjugates of this invention can be prepared by either direct conjugation of an agent to a conjugate moiety, wherein the resulting covalent bond is cleavable in vivo, or by covalently coupling a difunctionalized linker precursor with an agent to a conjugate moiety. The linker precursor is selected to contain at least one reactive functionality that is complementary to at least one reactive functionality on the agent and at least one reactive functionality on the conjugate moiety. Such complementary reactive groups are well known in the art as illustrated below:

COMPLEMENTARY BINDING CHEMISTRIES

| First Reactive Group | Second Reactive Group | Linkage |
|---|---|---|
| hydroxyl | carboxylic acid | ester |
| hydroxyl | haloformate | carbonate |
| thiol | carboxylic acid | thioester |
| thiol | haloformate | thiocarbonate |
| amine | carboxylic acid | amide |
| hydroxyl | isocyanate | carbamate |
| hydroxyl | haloformate | carbamate |
| amine | isocyanate | urea |
| carboxylic acid | carboxylic acid | anhydride |
| hydroxyl | phosphorus acid | phosphonate or phosphate ester |

In addition to the complementary chemistry of the functional groups on the linker to both the agent and conjugate moiety, the linker (when employed) is also selected to be cleavable in vivo. Cleavable linkers are well known in the art and are selected such that at least one of the covalent bonds of the linker that attaches the agent to the conjugate moiety can be broken in vivo thereby providing for the agent or active metabolite thereof to be available to the systemic blood circulation. The linker is selected such that the reactions required to break the cleavable covalent bond are favored at the physiological site in vivo which permits agent (or active metabolite thereof) release into the systemic blood circulation. The selection of suitable cleavable linkers to provide effective concentrations of the agent or active metabolite thereof for release into the systemic blood circulation can be evaluated using endogenous enzymes in standard in vitro assays to provide a correlation to in vivo cleavage of the agent or active metabolite thereof from the conjugate, as is well known in the art. It is recognized that the exact cleavage mechanism employed is not critical to the methods of this invention provided, of course, that the conjugate cleaves in vivo in some form to provide for the agent or active metabolite thereof for sustained release into the systemic blood circulation.

In another approach, a conjugate moiety and agent are each attached to moieties having mutual affinity for each (e.g., avidin or streptavidin and biotin, or hexahistidine and $Ni^{2+}$). In another approach, both agent and conjugate moiety are linked to a solid phase. Examples of such supports include nanoparticles (see, e.g., U.S. Pat. Nos. 5,578,325 and 5,543,158), molecular scaffolds, liposomes (see, e.g., Deshmuck, D. S., et al., *Life Sci.* 28:239–242 (1990), and Aramaki, Y., et al., *Pharm. Res.* 10:1228–1231 (1993), protein cochleates (stable protein-phospholipid-calcium precipitates; see, e.g. Chen et al., *J. Contr. Rel.* 42:263–272 (1996), and clathrate complexes. These supports can be used to attach other active molecules. Certain supports such as nanoparticles can also be used to encapsulate desired compounds. An agent can be linked to a support via a cleavable linkage allowing separation of the agent after uptake through a transporter.

Examples of cleavable linkers suitable for use as described above include nucleic acids with one or more restriction sites, or peptides with protease cleavage sites (see, e.g., U.S. Pat. No. 5,382,513). Other exemplary linkers that can be used are available from Pierce Chemical Company in Rockford, Ill.; suitable linkers are also described in EPA 188,256; U.S. Pat. Nos. 4,671,958; 4,459,839; 4,414,148; 4,699,784; 4,680,338, 4,569,789 and 4,590,071; and in Eggenweiler, H. M, *Drug Discovery Today*, 3: 552 (1998), each of which is incorporated in its entirety for all purposes.

There are many existing drugs for which uptake can be improved through the intestine. Drugs suitable for conversion to prodrugs that are capable of uptake from the intestine typically contain one or more of the following functional groups to which a promoiety may be conjugated: primary or secondary amino groups, hydroxyl groups, carboxylic acid groups, phosphonic acid groups, or phosphoric acid groups.

Examples of drugs containing carboxyl groups include, for instance, angiotensin-converting enzyme inhibitors such as alecapril, captopril, 1-[4-carboxy-2-methyl-2R,4R-pentanoyl]-2,3-dihydro-2S-indole-2-carboxylic acid, enalaprilic acid, lisinopril, N-cyclopentyl-N-[3-[(2,2-dimethyl-1-oxopropyl)thio]-2-methyl-1-oxopropyl]glycine, pivopril, quinaprilat, (2R, 4R)-2-hydroxyphenyl)-3-(3-mercaptopropionyl)-4-thiazolidinecarboxylic acid, (S) benzamido-4-oxo-6-phenylhexenoyl-2-carboxypyrrolidine, [2S-1[R*(R*))]]2α, 3αβ, 7αβ]-1[2-[[1-carboxy-3-phenylpropyl]-amino]-1-oxopropyl]octahydro-1H-indole-2-carboxylic acid, [3S-1[R*(R*))]], 3R*]-2-[2-[[1-carboxy-3-phenylpropyl]-amino]-1-oxopropyl]-1,2,3,4-tetrahydro-3-isoquinolone carboxylic acid, and tiopronin; cephalosporin antibiotics such as cefaclor, cefadroxil, cefamandole, cefatrizine, cefazedone, cefazuflur, cefazolin, cefbuperazone, cefixime, cefmenoxime, cefmetazole, cefodizime, cefonicid, cefoperazone, ceforanide, cefotaxime, cefotefan, cefotiam, cefoxitin, cefpimizole, cefpirome, cefpodoxime, cefroxadine, cefsulodin, cefpiramide, ceflazidime, ceftezole, ceftizoxime, ceftriaxone, cefuroxime, cephacetrile, cephalexin, cephaloglycin, cephaloridine, cephalosporin, cephanone, cephradine, and latamoxef; penicillins such as amoxycillin, anpicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, meziocillin, nafcillin, oxacillin, phenethicillin, piperazillin, sulbenicllin, temocillin, and ticarcillin; thrombin inhibitors such as argatroban, melagatran, and napsagatran; influenza neuraminidase inhibitors such as zanamivir and peramivir; non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclofenac, diflunisal, etodolac, fenbufen, fenclofenac, fenclosic acid, fenoprofen, ferobufen, flufenamic acid, flufenisal, flurbiprofin, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-11-oxodibenz[b,f]oxepin-2-yl) propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin $E_2$, 6,16-dimethylprostaglandin $E_2$, epoprostostenol, meteneprost, nileprost, prostacyclin, prostaglandins $E_1$, $E_2$, or $F_{2\alpha}$, and thromboxane $A_2$; quinolone antibiotics such as acrosoxacin, cinoxacin, ciprofloxacin, enoxacin, flumequine, naladixic acid, norfloxacin, ofloxacin, oxolinic acid, pefloxacin, pipemidic acid, and piromidic acid; other antibiotics such as aztreonam, imipenem, meropenem, and related carbopenem antibiotics.

Representative drugs containing amine groups include: acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, aminorex, aprinocid, cambendazole, cimetidine, cisapride, clonidine, cyclobenzadole, delavirdine, efegatrin, etintidine, fenbendazole, fenmetazole, flubendazole, fludorex, gabapentin, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, pregabalin, procainamide, ranitidine, tetrahydrazoline, tiamenidine, tinazoline, tiotidine, tocainide, tolazoline, tramazoline, xylometazoline, dimethoxyphenethylamine, N-[3(R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, carbidopa, clorprenaline, chlortermine, dopamine, L-Dopa, ephrinephrine etryptamine, fenfluramine, methyldopamine, norepincphrine, tocainide, enviroxime, nifedipine, nimodipine, triamterene, norfloxacin, and similar compounds such as pipedemic acid, 1-ethyl-6-fluoro-1, 4dihydro-4-oxo-7-(1-piperazinyl)-1,8-napthyridine-3-carboxylic acid, 1-cyclopropyl-6-fluoro-1, and 4-dihydro-4-oxo-7-(piperazinyl)-3-quinolinecarboxylic acid.

Representative drugs containing hydroxy groups include: steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosterone, and tigestol; tranquilizers such as dofexazepam, hydroxyzin, lorazepam, and oxazepam; neuroleptics such as acetophenazine, carphenazine, fluphenazine, perphenyzine, and piperaetazine; cytostatics such as aclarubicin, cytarabine, decitabine, daunorubicin, dihydro-5-azacytidine, doxorubicin, epirubicin, estramustin, etoposide, fludarabine, gemcitabine, 7-hydroxychlorpromazin, nelarabine, neplanocin A, pentostatin, podophyllotoxin, tezacitabine, troxacitabine, vinblastin, vincristin, and vindesin; hormones and hormone antagonists such as buserilin, gonadoliberin, icatibrant, and leuprorelin acetate; antihistamines such as terphenadine; analgesics such as diflunisal, naproxol, paracetamol, salicylamide, and salicyclic acid; antibiotics such as azidamphenicol, azithromycin, camptothecin, cefamandol, chloramphenicol, clarithromycin, clavulanic acid, clindamycin, demeclocyclin, doxycyclin, erythromycin, gentamycin, imipenem, latamoxef, metronidazole, neomycin, novobiocin, oleandomycin, oxytetracyclin, tetracycline, thiamenicol, and tobramycin; antivirals such as acyclovir, dideoxydidehydrocytidine, dideoxycytosine, 1-(2-deoxy-2-methylene-beta-D-erythro-pentofuranosyl)cytidine, fluoro-dideoxydidehydrocytidine, fluorodideoxycytosine, FMAU (1-(2-deoxy-2-fluoro-beta-D-arabinofuranosyl)thymine), deoxy-5-fluoro-3'-thiacytidine, 2'-fluoro-ara-dideoxyinosine, ganciclovir, lamivudine, penciclovir, SddC, stavudine, 5-trifluoromethyl-2'-deoxyuridine, zalcitabine, and zidovudine; bisphosphonates such as EB-1053 (1-hydroxy-3-(1-pyrrolidinyl)propylidene-1,1-bisphosphonate), etidronate, ibandronate, olpadronate, residronate, 1-hydroxy-2-(imidazo[1,2-a]pyridin-3-yl)ethylidene]-bisphosphonic acid, and zolendronate; protease inhibitors such as ciprokiren, enalkiren, ritonavir, saquinavir, and terlakiren; prostaglandins such as arbaprostil, carboprost, misoprostil, and prostacydin; antidepressives such as 8-hydroxychlorimipramine and 2-hydroxyimipramine; antihypertonics such as sotarol and fenoldopam; anticholinerogenics such as biperidine, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon, and triamcinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon, and pentazocin; stimulants such asmazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol, and timolol; α-sympathomimetics such as adrenalin, metaraminol, midodrin, norfenefrin, octapamine, oxedrin, oxilofrin, oximetazolin, and phenylefrin; β-sympathomimetics such as bamethan, clenbuterol, fenoterol, hexoprenalin, isoprenalin, isoxsuprin, orciprenalin, reproterol, salbutamol, and terbutalin; bronchodilators such as carbuterol, dyphillin, etophyllin, fenoterol, pirbuterol, rimiterol and terbutalin; cardiotonics such as digitoxin, dobutamin, etilefrin, and prenalterol; antimycotics such as amphotericin B, chlorphenesin, nystatin, and perimycin; anticoagulants such as acenocoumarol, dicoumarol, phenprocoumon, and warfarin; vasodilators such as bamethan, dipyrimadol, diprophyllin, isoxsuprin, vincamin and xantinol nicotinate; antihypocholesteremics such as compactin, eptastatin, mevinolin, and simvastatin; miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), quetiapine (CNS), serotonin (neurotransmitter), and silybin (hepatic disturbance).

Representative drugs containing phosphonic acid moieties include: adefovir, alendronate, (N6-[2-methylthio) ethyl]-2-[3,3,3-trifluoropropylthio]-5'-adenylic acid, BMS-187745 (a squalene synthase inhibitor from Bristol-Meyers Squibb Inc.), ceronapril, CGP-24592 (Novartis, Inc.), DL-(E)-2-amino-4-methyl-5-phosphono-3-pentenoic acid; 4-methyl-APPA, CGP-39551 (ethyl esters of (DL-[E]-2-amino-4-methyl-5-phosphono-3-pentenoic acid)), CGP-40116 (a competitive NMDA antagonist by Novartis Inc.), cidofovir, clodronate, EB-1053 (1-hydroxy-3-(1-pyrrolidinyl)propylidene-1,1-bisphosphonate), etidronate, fanapanel, foscarnet, fosfomycin, fosinopril, fosinoprilat, ibandronate, midafotel, neridronate, olpadronate, pamidronate, residronate, tenofovir, tiludronate, [2-(8,9-dioxo-2,6-diazabicyclo[5.2.0]non-1(7)-en-2-yl)ethyl] phosphonic acid, 1-hydroxy-2-(imidazo[1,2-a]pyridin-3-yl) ethylidene]-bisphosphonic acid, and zolendronate.

Representative drugs containing phosphoric acid moieties include: bucladesine, choline alfoscerate, citocoline, fludarabine phosphate, fosopamine, GP-668, perifosine, triciribine phosphate, and phosphate derivatives of nucleoside analogs which require phophorylation for activity, such as lamivudine, acyclovir, azidothymidine, E-5-(2-bromovinyl)-2'-deoxyuridine, dideoxycytosine, dideoxyinosine, FMAU (1-(2-deoxy-2-fluoro-beta-D-arabinofuranosyl)thymine), deoxy-5-fluoro-3'-thiacytidine, ganciclovir, gemcitabine, (R)-9-[4-Hydroxy-2-(hydroxymethy)butyl]guanine, lamivudine, penciclovir and the like.

Preferred drugs for modification to prodrugs capable of intestinal absorption and incorporation into sustained release formulations include the following compounds: analgesics and/or antiinflammatory agents selected from the group consisting of acetaminophen, buprenorphine, diclofenac, diflunisal, fenoprofen, ibuprofen, indomethacin, ketoprofen, mefenamic acid, meptazinol, morphine, oxycodone, pentazocine, pethidine, tolmetin, and tramadol; antihypertensive agents selected from the group consisting of captopril, diltiazem, methyldopa, metoprolol, prazosin, propranolol, quinapril, sotalol, and timolol; antibiotic agents selected from the group consisting of amoxicillin, ampicillin, aztreonam, cefaclor, cefadroxil, cefixime, cefotaxime, cefoxitin, cefpodoxime, ceftizoxime, ceftriaxone, cefuroxime, cephalexin, ciproflaxacin, clindamycin, erythromycin, imipenem, mandol, meropenem, metronidazole, and tobramycin; antiviral agents selected from the group consisting of acyclovir, delavirdine, didanosine, foscarnet, ganciclovir, indinavir, lamivudine, nelfinavir, penciclovir, ritonavir, saquinavir, stavudine, zalcitabine, and zidovudine; bronchodilator and or anti-asthmatic agents selected from the group consisting of salbutamol and terbutaline; antiarrhythmic agents selected from the group consisting of mexiletine, procainamide, and tocainide; centrally acting substances selected from the group consisting of baclofen, benserazide, bupropion, carbidopa, gabapentin, levodopa, methylphenildate, pramipexole, pregabalin, quetiapine, ropinirole, and vigabatrin; cytostatics and metastasis inhibitors selected from the group consisting of cytarabine, decitabine, docetaxal, flutamide, gemcitabine, paclitaxel, and pentostatin; and, agents for treatment of gastrointestinal disorders selected from the group consisting of cisapride, metoclopramide, and misoprostol.

6. Pharmaceutical Compositions and Methods of Treatment

Agents that are themselves substrates for PEPT2 or which are linked to conjugate moieties that are substrates for PEPT2 can be can be incorporated into pharmaceutical compositions. Usually, although not necessarily, such pharmaceutical compositions are designed for oral administration. Oral administration of such compositions results in uptake through the intestine via the PEPT2 and entry into the systemic circulation. The pharmaceutical composition can thus be efficiently delivered to a wide range of tissues in the body. The specificity of compositions for PEPT2 renders the compositions susceptible to uptake by the brain (including the choroid plexus) and kidney that express PEPT2 at high levels. However, the methods are also useful for treating a wide variety of diseases in patients who are free of diseases of the brain, kidney, lung, and spleen in which PEPT2 is expressed to a significant extent. In such methods, the expression of PEPT2 in the kidney increase reabsorption of the pharmaceutical composition into the systemic circulation thereby increasing its half life and thereby reducing the dosage necessary. In some methods, the agent or conjugate moiety is a substrate for both PEPT2 and PEPT1. In some methods, the agent or conjugate moiety is a substrate for PEPT2 and is not a substrate, or is a poor substrate, for PEPT1.

Agents optionally linked to a conjugate moiety are combined with pharmaceutically-acceptable, non-toxic carriers of diluents, which are defined as vehicles commonly used to formulate pharmaceutical compositions for animal or human administration. The diluent is selected so as not to adversly affect the biological activity of the combination. Examples of such diluents are distilled water, buffered water, physiological saline, PBS, Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., "Remington's Pharmaceutical Sciences", Mace Publishing Company, Philadelphia, Pa., 17th ed. (1985); for a brief review of methods for drug delivery, see, Langer, Science 249:1527–1533 (1990); each of these references is incorporated by reference in its entirety).

Pharmaceutical compositions for oral administration can be in the form of e.g., tablets, pills, powders, lozenges, sachets, cachets, elixirs, suspensions, emulsions, solutions, or syrups. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. Preserving agents such as methyl- and propylhydroxy-benzoates; sweetening agents; and flavoring agents can also be included. Depending on the formulation, compositions can provide quick, sustained or delayed release of the active ingredient after administration to the patient. The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active agent.

The compositions can be administered for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, compositions are administered to a patient susceptible to or otherwise at risk of a particular disease or infection. Hence, a "prophylactically effective amount" is an amount sufficient to prevent, hinder or retard a disease state or its symptoms. In either instance, the precise amount of compound contained in the composition depends on the patient's state of health and weight.

An appropriate dosage of the pharmaceutical composition is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The pharmaceutical compositions can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. The route of administration depends in part on the chemical composition of the active compound and any carriers.

The components of pharmaceutical compositions are preferably of high purity and are substantially free of potentially harmful contaminants (e.g., at least National Food (NF) grade, generally at least analytical grade, and more typically at least pharmaceutical grade). To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions. Compositions for oral administration need not be sterile or substantially isotonic but are usually made under GMP conditions.

EXAMPLES

1. PCR Analysis of Transporter Expression

Oligonucleotide primers were designed to amplify specific sequences in either human PEPT1 (2 sets using Genbank) or PEPT2 (2 sets using Genbank). The forward and reverse primer sequences were (PEPT1#1 F-catgcaccaccacgcccagctatttt (SEQ ID NO:3) and R-gcgcggtagctcaagcctgtaatccc (SEQ ID NO:4) which amplifies 147 base pairs in the 3'UTR, PEPT1#2 F-ccgcgttgcttctggtcgtctgtgta (SEQ ID NO:5) and R-tccatcctccacttgcctcctgacct (SEQ ID NO:6) which amplifiers 197 base pairs across the stop codon; PEPT2#1 F-acaaccaatgggatgacaaccgtgag (SEQ ID NO:7) and R-aggcagatcaccagcaggaggcagga (SEQ ID NO:8) which amplifiers 533 base pairs in the PEPT2 open reading frame; PEPT2#2 F-caatgttggtgaagactatggtgtgt (SEQ ID NO:9) and R-aacaagcacgatgatattcccaactg (SEQ ID NO:10) which amplifiers the least 376 base pairs in the PEPT2 open reading frame). All primers had annealing temperatures above 55° C. and products were sequenced to verify specificity.

Transporter expression was quantitated by PCR (polymerase chain reaction) amplification using real-time PCR (Cepheid Smartcycler PCR instrument and Perkin-Elmer SYBR-green reagents; all protocols per manufacturers specifications). Single-stranded cDNA was prepared from human mRNA (purchased from Clontech, BioChain, and Stratagene) or differentiated Caco-2 cells (Qiagen RNA purification columns) using Thermoscript (Stratagene) reverse transcriptase kit. Real-time PCR was performed using the primer sets listed above to amplify fragments of human PEPT1 or PEPT2. In addition, total mRNA abundance was normalized by measurement of β-Actin levels in each tissue (Clontech primer set). Transcript abundance was measured by determining the threshold cycle for PEPT1 or PEPT2 and calculating transcript number using a calibration factor derived from amplification of known plasmid copy numbers. To compare different tissues, all data are expressed as a fraction of β-actin transcript levels.

Table 1 shows expression levels of PEPT1 and PEPT2 mRNA expressed as a percentage of the expression level of beta actin mRNA in the same tissue. It can be seen that substantial expression of PEPT2 is obtained in the human jejunwn, ileum, ileocecum, and cecum and detectable expression in several other intestinal tissues. Levels of expression in the rat duodenumn, jejunum and ileum and colon were barely detectable.

TABLE 1

Expression of PEPT1 and PEPT2 in Various Tissues and Cell lines

|  |  | Sto | Eso | Duo | Jej | Ile | Il-Ce | Cec | Acol | Tcol | Dcol | Hea | Bra | Lun | SMus | Kid | Pan |
|---|---|---|---|---|---|---|---|---|---|---|---|---|---|---|---|---|---|
| PEPT1 | U13173 | 18.96 | 2.97 | 4.92 | 4.52 | 3.74 | 1.13 | 0.28 | 0.31 | 5.27 | 12.12 | 5.27 | 8.25 | 0.00 | 16.68 | 5.62 | 7.26 |
| PEPT2 | NM_021082 | 0.05 | 0.01 | 0.10 | 0.77 | 0.52 | 0.29 | 0.11 | 0.07 | 0.01 | 0.01 | 0.01 | 0.09 | 0.08 | 0.01 | 1.14 | 0.46 |

|  |  |  |  |  |  |  |  |  | Caco-2 | HCT28 | | HT29 | |
|---|---|---|---|---|---|---|---|---|---|---|---|---|---|
|  |  | Liv | Thy | Spl | Leu | Pla | Pros | Test | Ova | Diff. | Undiff. | Diff. | Undiff. | Diff |
| PEPT1 | U13173 | 4.08 | 12.12 | 21.54 | 24.48 | 12.12 | 0.00 | 0.00 | 10.00 | 3.31 | 30.24 | 16.63 | 3.06 | 2.78 | 9.18 | 77.43 |
| PEPT2 | NM_021082 | 0.00 | 0.03 | 0.09 | 0.02 | 0.01 | 0.53 | 0.11 | 0.00 | 0.09 | 0.76 | 0.26 | 0.01 | 0.18 | 0.01 | 0.64 |

GB#=GenBank accession number
Sto=stomach
Eso=esophogus
Duo=duodenum
Jej=jejunum
Ile=ileum
Il-Ce=ileum-cccum valve.
Cec=cecum
Acol=ascending colon
Tcol=total colon
Dcol=descending colon
Hea=heart
Bra=Brain
Lun=lung
SMus=smooth muscle
Kid=kidney
Pan=pancreas
Liv=liver
thy=thymus
spl=spleen
Leu=leukocytes
Pla=platelets
Pros=prostate
test=testes
Ova=ovaries 2. Functional Analysis of PEPT1 and PEPT2

The complete open reading frame was cloned into a *Xenopus* oocyte expression plasmid, linearized, and cRNA was generated by run-off transcription using the T7 polymerase. *Xenopus* oocytes were prepared and maintained as previously described (Collins, et al., 1997) and injected with 10–30 ng RNA. Transport currents were measured 2–4 days after injection using two-electrode voltage-clamp (Axon Instruments). All experiments were performed using a modified oocyte Ringers solution (90 mM NaCl, 2 mM KCl, 1.8 mM CaCl2, 1 mM MgCl2, and 10 mM NaHEPES, pH 6.8). The membrane potential of oocytes was held at −60 mV and current traces acquired using PowerLab software. Responses to compounds were measured in the presence and absence of a specific non-transported inhibitor (XP10973) for PEPT1 and PEPT2. Data are expressed as the currents that are blocked by XP10973

Stable clones of CHOK1 cells were obtained by electroporation, selection in G418, and sorting into single-clones using flow-activated cell sorting (Cytomation). Stable clones expressing PEPT1 or PEPT2 were identified by enhanced uptake of radiolabeled Gly-Sar. For cell uptake studies, CHOK1 clones were seeded into polylysine coated 96-well microtitre plates and grown for 2–3 days. Cells were incubated with experimental solutions (combinations of radiolabeled and unlabeled compounds) for 30 minutes, washed four times, and either lysed in scintillation solution or water. Uptake of unlabeled compounds was quantitated by LC/MS/MS.

Table 2 shows the Vmax of several commercial compounds in oocytes transfected with PEPT1 or PEPT2 compared with Vmax of control Gly-Sar. The table also shows Vmax in the presence of the inhibitor XP10973.

XP10973

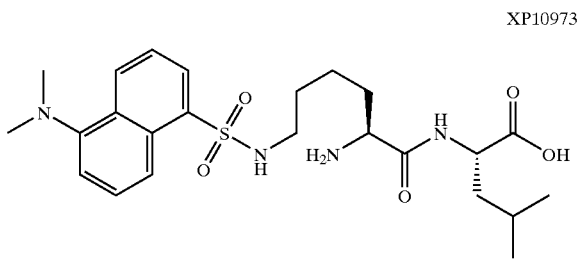

XP10973 is a specific inhibitor of both PEPT1 and PEPT2. It can be seen that cephradine, cephadroxil, cefaclor and amoxacillin are relatively poor susbstrates relative to Gly-Sar for cells transfected with PEPT1. However, these compounds have Vmax's comparable to or greater than that of Gly-Sar for cells transfected with PEPT2 indicating that the compounds are relatively good substrates for PEPT2. This conclusion is reinforced by the data in the presence of the XP10973 inhibitor. The result that XP10973 inhibits transport in both PEPT1 and PEPT2 transfected cells indicates that transport in such cells is at least in part due to the PEPT1 and PEPT2 transporters respectively. The smaller extent of inhibition for most substrates for PEPT1 relative to PEPT2 indicates that nonspecific transport mechanisms make a more significant relative contribution in the cells transfected with PEPT1. Except for cephadroxil, treatment with XP1097 results in a lesser percentage decrease in Vmax for oocytes transfected with PEPT1 relative to oocytes transfected with PEPT2. In short, the experiment shows that cefaclor, cefadroxil and cephradine are better substrates for PEPT2 than they are for PEPT1. Because it is known that the commercial compounds are orally available, it is probable that they are taken up through the mechanism by an alternate transporter, such as PEPT2.

TABLE 2

| Drug | PEPT1 (% Gly-Sar) | | PEPT2 (% Gly-Sar) | |
|---|---|---|---|---|
|  | drug only | +XP10973 | drug only | +XP10973 |
| Gly-Sar | 100 | 16 | 100 | 12 |
| Cephradine | 3.5 | 1.9 | 159 | 37 |
| Cephadroxil | 18 | 2.1 | 96 | 27 |
| Cefaclor | 4 | 1.6 | 148 | 22 |
| Amoxacillin | 1.3 | 1.1 | 85 | 15 |

3. Analysis of Uptake in Differentiated Caco-2 Cells

Caco-2 cells were plated on Millipore transwell filters and allowed to differentiate for 18–22 days. Integrity of the monolayers was confirmed by lack of radiolabeled inulin transport across the monolayer. Compounds were added to the apical chamber, and the appearance of compounds in the basolateral chamber were measured at various timepoints by scintillation counting or LC/MS/MS.

Figure 2:
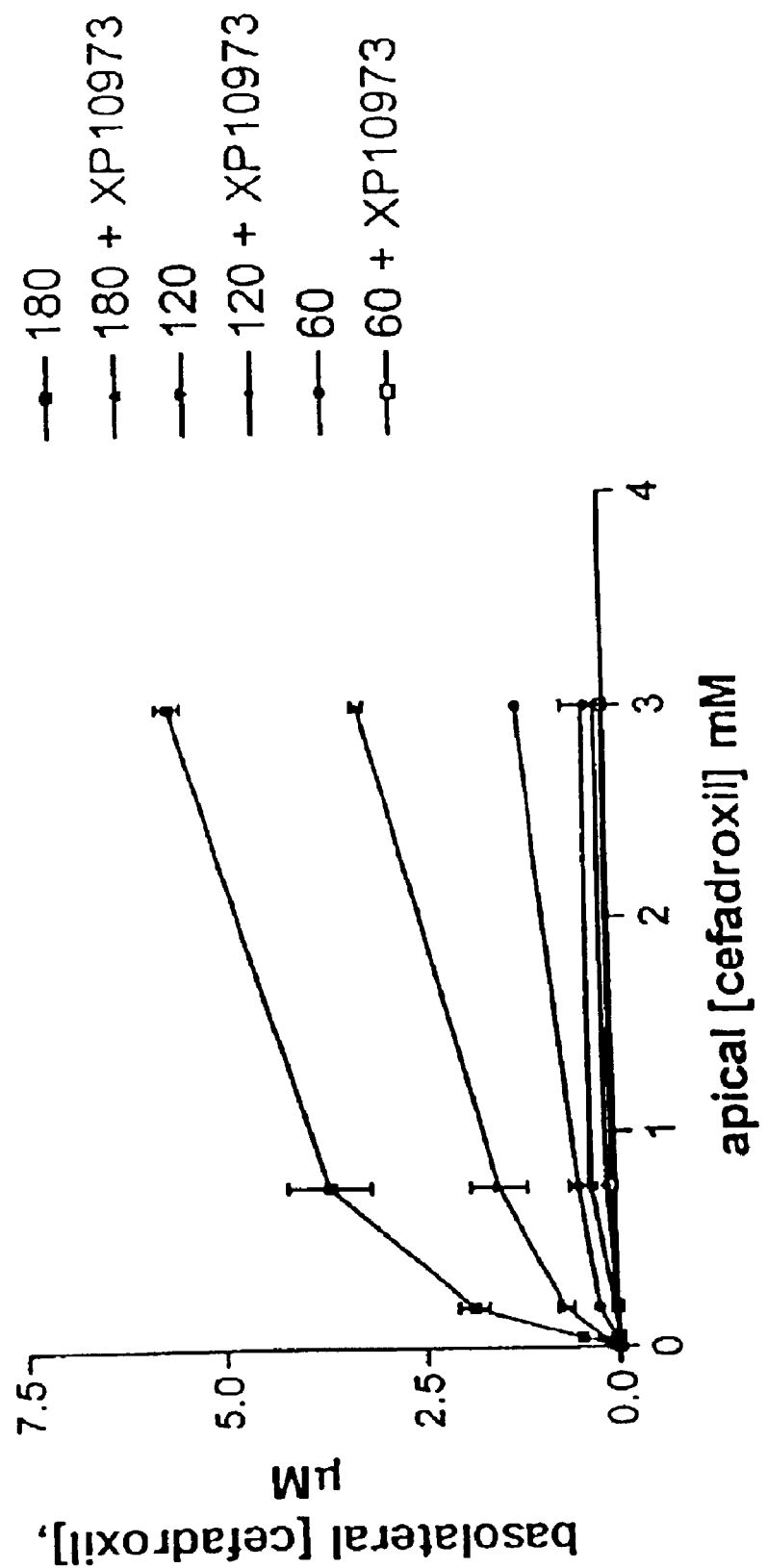
FIG. 2 shows uptake of cefadroxil by Caco-2 cells.

FIGS. 1 and 2 show uptake of cephradine and cefadroxil by Caco-2 cells in the presence and absence of XP10973 inhibitor. As shown in Table 1, Caco-2 cells express both the PEPT1 and PEPT2 transporters. However, as described above, cephradine and cefadroxil are poor substrates for PEPT1 and good substrates for PEPT2. The figures show that both cephradine and cefadroxil are taken up by the Caco-2 cells and that uptake is inhibited by XP10973. It can be inferred from these results that the cephradine and cefadroxil are taken up via the PEPT2 transporter.

4. Procedure for Preparing a Library to Explore for PEPT2 Specific Substrates

Figure 3:
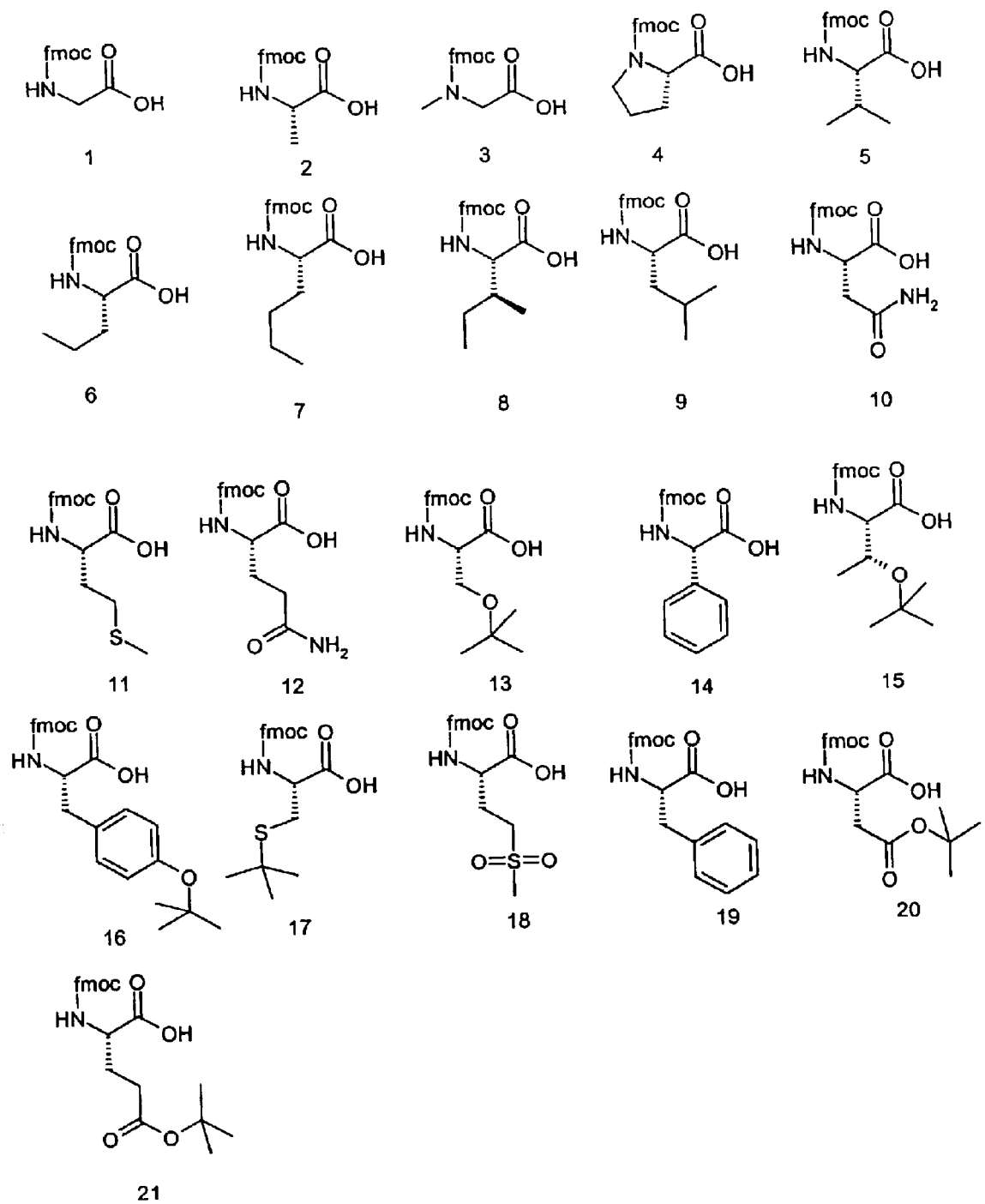
FIG. 3 shows F moc-amino acids.
Figure 4:
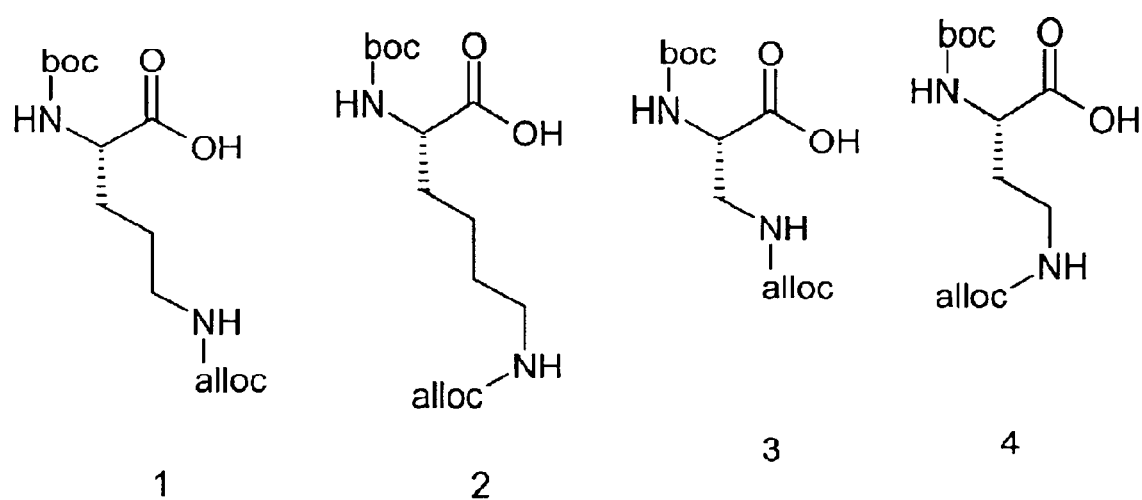
FIG. 4 shows Boc-Alloc amino acids.
Figure 5:
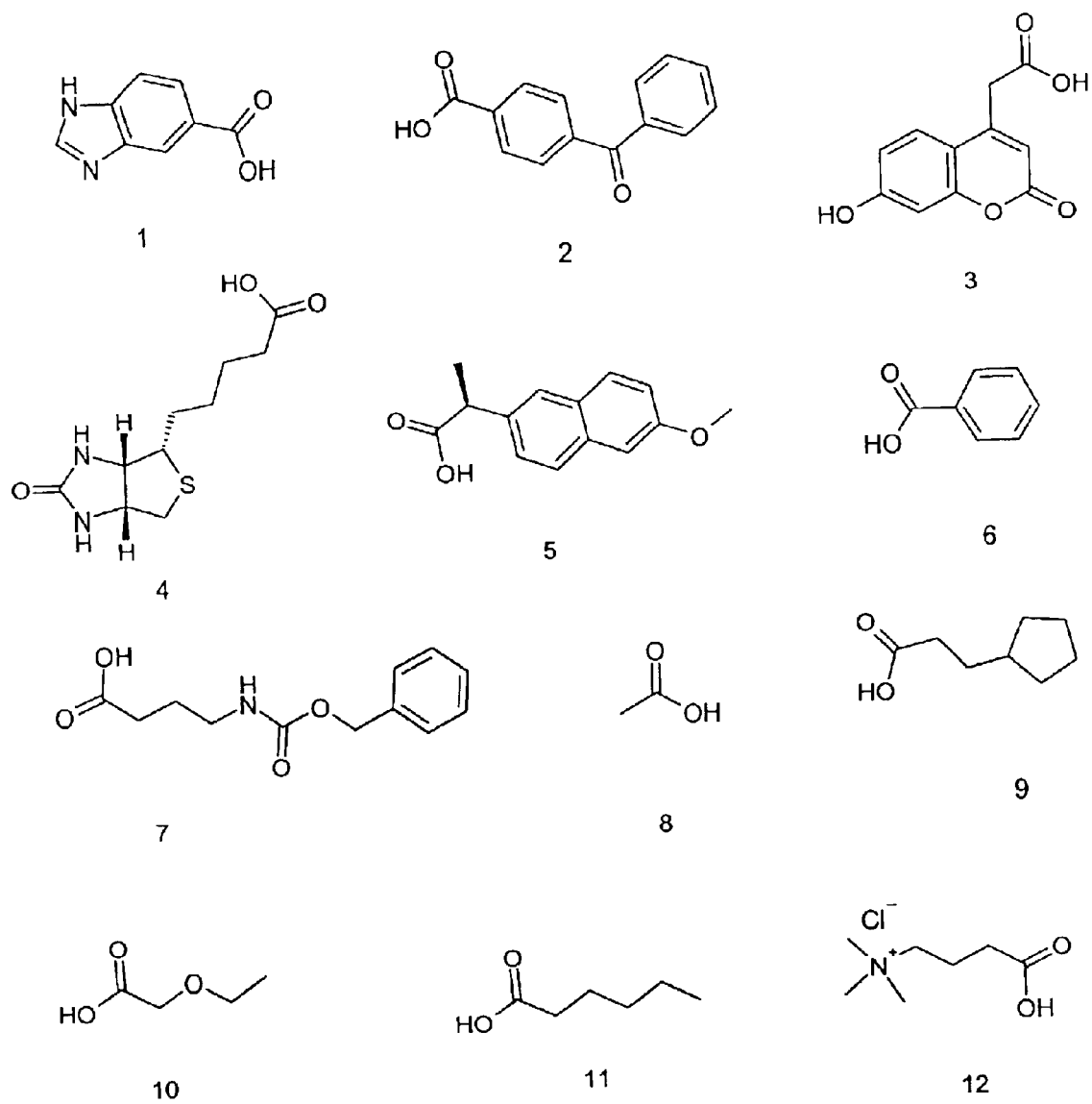
FIG. 5 shows carboxylic acid.

Into twenty-one 50 ml Altech tubes is added Polystyrene-chlorotritylchloride resin (5 g to each), dichloromethane (25 mL), and 3 equivalents of F moc-amino acids (see FIG. 3 for structures), and 6 equivalents of diethylisopropylamine. The reactions are shaken at room temperature for 30 minutes. The resins are drained and washed with methanol (2×), dichloromethane (3×), and N,N-dimethylformamide (3×). The resins are then treated with 20% piperidine in N,N-dimethylformamide for 1 hour. The resins are drained and washed with methanol (2×), dichloromethane (3×), and N,N-dimethylformamide (3×). Each resin is divided into four 25 mL Alltech tubes, and N,N-dimethylformamide (10 mL) was added. To each of the four different tubes was added a mixture of 5 equivalents of Boc-Alloc amino acids (FIG. 4), 5 equivalents of HATU, and 10 equivalents of diethylisopropylamine, in 10 mL of N,N-dimethylformamide. The reactions are shaken at ambient temperature for 20 hours. The resins are drained and washed with methanol (2×), dichloromethane (3×), and N,N-dimethylfonnamide (3×). Each resin is treated with 0.1 equivalents of tetrakis(triphenylphosphine)palladium(0) in N,N-dimethylformamide (10 mL) for 20 hours to effect the alloc deprotection. The resins are drained and washed with methanol (2×), dichloromethane (3×), and N,N-dimethylformamide (3×). Each resin is divided into twelve 4 mL Alltech tubes, and dichloromethane (1 mL) was added. To each of the twelve different tubes is added a mixture of 5 equivalents of carboxylic acid (FIG. 5), 5 equivalents of HATU, and 10 equivalents of diethylisopropylamine, in 1 mL of N,N-dimethylformamide. The reactions are shaken at ambient temperature for 20 hours. The resins are drained and washed with methanol (2x), dichloromethane (3x), N,N-dimethylformamide (3x) and dichloromethane (3x). The resulting 1008 tubes were treated with 90% trifluoroacetic acid in dichloromethane (0.5 mL) for 3 hours, the tubes are drained into eleven 2 mL 96 deep well plates. The solvent is removed under reduced pressure using a GeneVac. The resulting residues were dissolved in DMSO to an approximate concentration of 100 mM and submitted for biological assay to test for capacity to be transported via PEPT2 (e.g., using oocytes transfected with PEPT2 as described above).

5. Procedure for Preparing a Library to Explore for PEPT2 Specific Substrates

Figure 6:
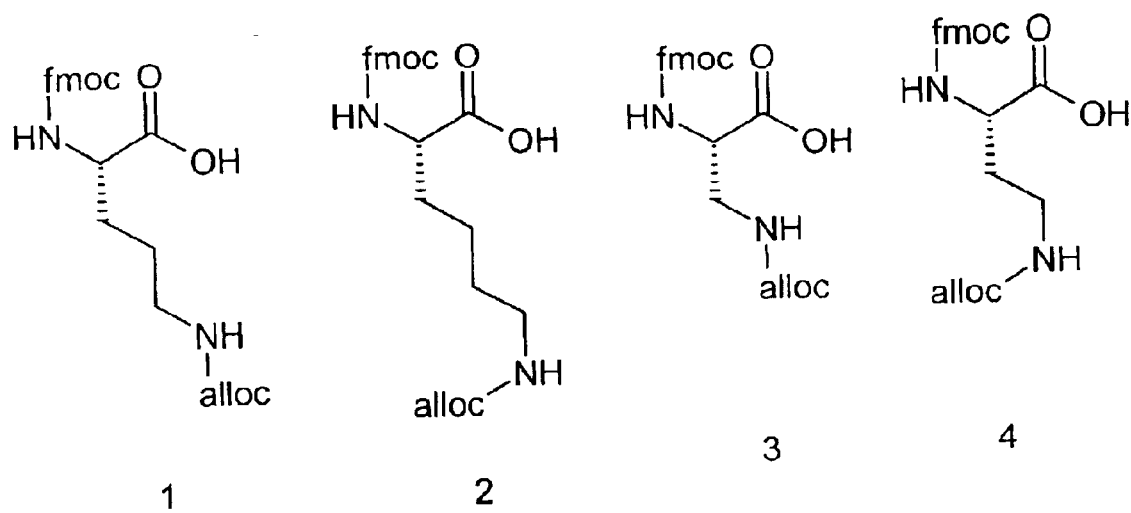
FIG. 6 shows Fmoc-alloc-amino acids.
Figure 7:
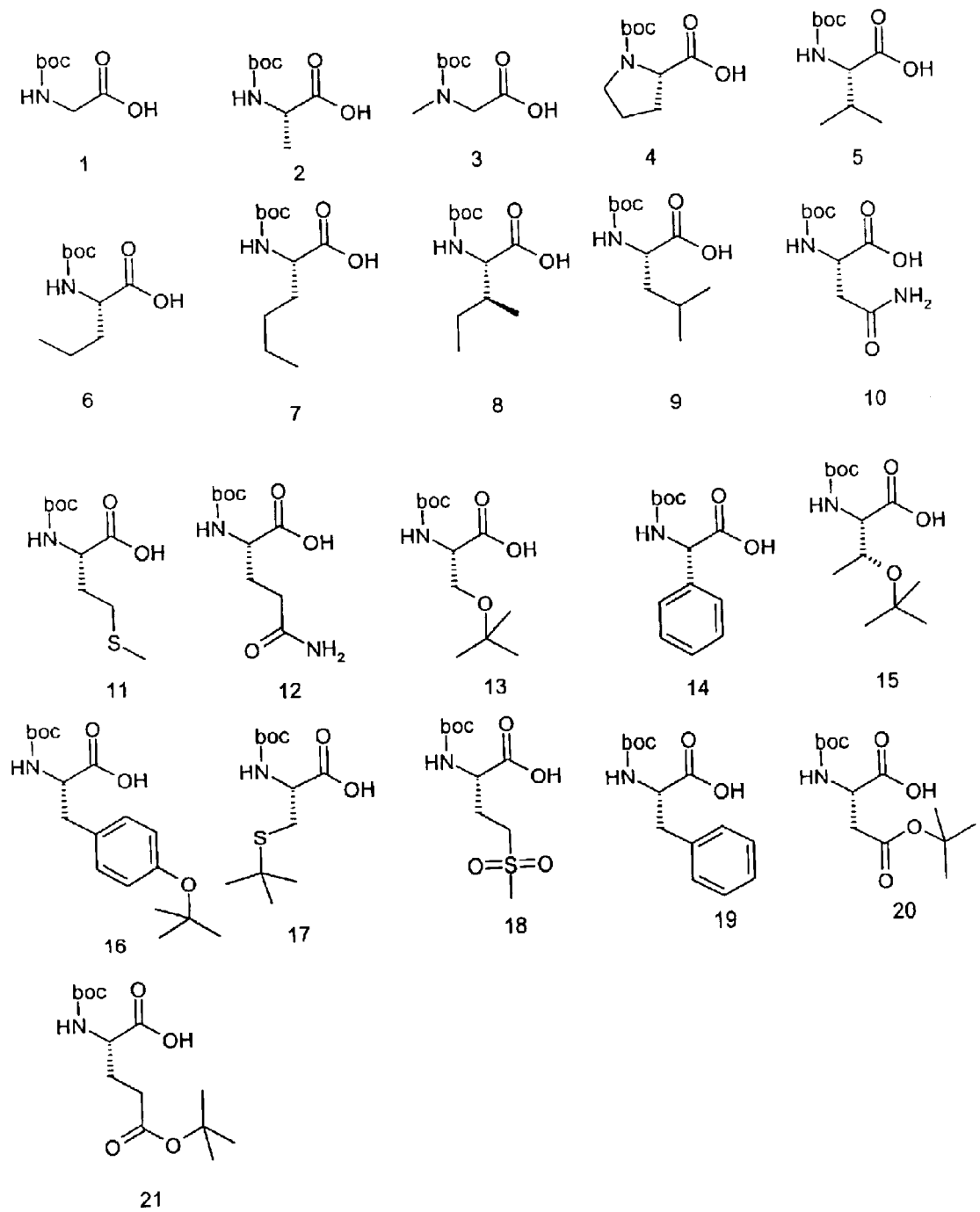
FIG. 7 shows Boc-amino acids.

Into four 250 mL peptide vessels is added Polystyrene-chlorotritylchloride resin (20 g to each), dichloromethane 125 mL), and 3 equivalents of Fmoc-alloc-amino acids (see FIG. 6 for structures), and 6 equivalents of diethylisopropylamine. The reactions are shaken at room temperature for 30 minutes. The resins are drained and washed with methanol (2x), dichloromethane (3x), and N,N-dimethylformamide (3x). The resins are then treated with 20% piperidine in N,N-dimethylformamide for 1 hour. The resins are drained and washed with methanol (2x), dichloromethane (3x), and N,N-dimethylformamide (3x). Each resin is divided into twenty-one 25 mL Alltech tubes, and N,N-dimethylformamide (10 mL) is added. To each of the four different tubes is added a mixture of 5 equivalents of Boc-amino acids (FIG. 7), 5 equivalents of HATU, and 10 equivalents of diethylisopropylamine, in 10 mL of N,N-dimethylformamide. The reactions are shaken at ambient temperature for 20 hours. The resins are drained and washed with methanol (2x), dichloromethane (3x), and N,N-dimethylformamide (3x). Each resin is treated with 0.1 equivalents of tetrakis(triphenylphosphine)palladium(0) in N,N-dimethylformamide (10 mL) for 20 hours to effect the alloc deprotection. The resins are drained and washed with methanol (2x), dichloromethane (3x), and N,N-dimethylformamide (3x). Each resin is divided into twelve 4 mL Alltech tubes, and dichloromethane (1 mL) was added. To each of the twelve different tubes is added a mixture of 5 equivalents of carboxylic acid (FIG. 5), 5 equivalents of HATU, and 10 equivalents of diethylisopropylamine, in 1 mL of N,N-dimethylformamide. The reactions are shaken at ambient temperature for 20 hours. The resins are drained and washed with methanol (2x), dichloromethane (3x), N,N-dimethylformamide (3x) and dichloromethane (3x). The resulting 1008 tubes are treated with 90% trifluoroacetic acid in dichloromethane (0.5 mL) for 3 hours, the tubes were drained into eleven 2 mL 96 deep well plates. The solvent is removed under reduced pressure using a GeneVac. The resulting residues were dissolved in DMSO to an approximate concentration of 100 mM and submitted for biological assay to test for capacity to be transported via PEPT2 (e.g., using oocytes transfected with PEPT2 as described above).

What is claimed is:

1. A method of screening a conjugate or conjugate moiety for transport by a PEPT2 transporter, comprising:

providing a cell expressing a PEPT2 transporter, wherein the PEPT2 transporter has the amino acid sequence of SEQ ID NO:2 or has at least 90% sequence identity thereto, and the PEPT2 transporter can transport Gly-Sar;

contacting the cell with a conjugate or conjugate moiety in vitro; and determining whether the conjugate or conjugate moiety passes into and/or through the cell by way of the transporter.

2. The method of claim 1, wherein the cell is transfected with DNA encoding the PEPT2 transporter.

3. The method of claim 1, wherein the cell is an oocyte injected with a nucleic acid encoding PEPT2 transporter.

4. The method of claim 1, wherein the cell has no detectable PEPT1 receptor.

5. The method of claim 1, wherein the method further screens the conjugate or conjugate moiety for transport by a PEPT1 transporter, the method further comprising providing a second cell expressing a PEPT1 transporter and lacking a PEPT2 transporter, wherein the PEPT1 transporter has the amino acid sequence of SEQ ID NO:1, or has at least 90% sequence identity thereto, and the PEPT1 transporter can transport Gly-Sar;

contacting the second cell with the conjugate or conjugate moiety; and determining whether the conjugate or conjugate moiety passes into and/or through the second cell by way of the PEPT1 transporter.

6. The method of claim 5, wherein the conjugate or conjugate moiety is contacted with the second cell before being contacted with the first cell.

7. The method of claim 5, wherein the method determines that the conjugate or conjugate moiety is transported by PEPT2 and not by PEPT1.

8. The method of claim 1, further comprising incorporating the conjugate or conjugate moiety into a pharmaceutical composition suitable for oral delivery, if the conjugate or conjugate moiety passes into and/or through the cell.

9. The method of claim 1, wherein the method screens the conjugate and determines that the conjugate has a Vmax for the PEPT2 transporter of at least 100% of the Vmax of substrate Gly-Sar for PEPT2.

10. The method of claim 1, further comprising contacting the conjugate or conjugate moiety with a control cell having transporters other than the PEPT2 transporter, and wherein the determining step determines whether the agent, conjugate or conjugate moiety passes into and/or through the cell relative to the control cell, passage into and/or through the cell relative to the control cell indicating that the conjugate or conjugate moiety is a substrate for PEPT2.

11. A method of screening an agent, conjugate or conjugate moiety for transport by a PEPT2 transporter, comprising:

providing a cell expressing a PEPT2 transporter, wherein the PEPT2 transporter has the amino acid sequence of SEQ ID NO:2 or has at least 90% sequence identity thereto, and the PEPT2 transporter can transport Gly-Sar;

contacting the cell with an agent, conjugate or conjugate moiety in vitro, wherein the agent, conjugate or conjugate moiety has a Vmax less than 1% of the Vmax of Gly-Sar for a PEPT1 transporter, wherein the PEPT1 transporter has the amino acid sequence of SEQ ID NO:1, or has at least 90% sequence identity thereto, and the PEPT1 transporter can transport Gly-Sar; and determining whether the agent, conjugate or conjugate moiety passes into and/or through the cell by way of the transporter.

12. The method of claim 11, further comprising contact the agent, conjugate or conjugate moiety with a control cell having transporters other than the PEPT2 transporter, and wherein the determining step determines whether the agent, conjugate or conjugate moiety passes into and/or through the cell relative to the control cell, passage into and/or through the cell relative to the control cell indicating that the conjugate or conjugate moiety is a substrate for PEPT2.

* * * * *